US008337493B2

(12) United States Patent
Sohn

(10) Patent No.: US 8,337,493 B2
(45) Date of Patent: Dec. 25, 2012

(54) HANDHELD TRANSDERMAL DRUG DELIVERY AND ANALYTE EXTRACTION

(75) Inventor: Ze'ev Sohn, Ginot Shomron (IL)

(73) Assignee: Syneron Medical Ltd, Yokneam Illit (IL)

(*) Notice: Subject to any disclaimer, the term of this patent is extended or adjusted under 35 U.S.C. 154(b) by 0 days.

(21) Appl. No.: 13/013,413

(22) Filed: Jan. 25, 2011

(65) Prior Publication Data
US 2011/0178518 A1 Jul. 21, 2011

Related U.S. Application Data

(63) Continuation of application No. 10/511,966, filed as application No. PCT/IL03/00314 on Apr. 15, 2003, now abandoned.

(60) Provisional application No. 60/374,224, filed on Apr. 19, 2002.

(51) Int. Cl.
*A61B 18/18* (2006.01)
(52) U.S. Cl. ......................................................... 606/45
(58) Field of Classification Search .................. 606/41
See application file for complete search history.

(56) References Cited

U.S. PATENT DOCUMENTS

| | | | |
|---|---|---|---|
| 3,964,482 A | 6/1976 | Gerstel et al. | |
| 4,755,361 A | 7/1988 | Fuderer | |
| 4,837,027 A | 6/1989 | Lee et al. | |
| 4,943,290 A | 7/1990 | Rexroth et al. | |
| 5,019,034 A | 5/1991 | Weaver et al. | |
| 5,165,418 A | 11/1992 | Tankovich | |
| 5,196,709 A | 3/1993 | Berndt et al. | |
| 5,232,441 A | 8/1993 | Stephen et al. | |
| 5,246,867 A | 9/1993 | Lakowicz et al. | |

(Continued)

FOREIGN PATENT DOCUMENTS

EP 547482 A1 6/1993

(Continued)

OTHER PUBLICATIONS

A Supplementary European Search Report dated Apr. 29, 2011, which issued during the prosecution of Applicant's EP 06 75 6211.

(Continued)

*Primary Examiner* — Theodore Stigell
*Assistant Examiner* — Jason Flick
(74) *Attorney, Agent, or Firm* — Smith Risley Tempel Santos LLC; Gregory Scott Smith

(57) ABSTRACT

Apparatus (20) for application to skin of a subject is provided. The apparatus includes a board (30) having a first surface and a second surface, the first surface including a plurality of ablation electrodes (41), which are adapted to be applied to the skin, and the second surface including one or more contact pads (32), each one of the contact pads electrically coupled to at least one of the ablation electrodes. The apparatus further includes one or more driving electrodes (28). An energy applicator (e.g., motor 22), coupled to the driving electrodes, is adapted to pass the driving electrodes over the contact pads. A power source (e.g., power unit 102) is adapted to drive a current from the driving electrodes, to the contact pads, and to the ablation electrodes. The current is capable of ablating at least a portion of stratum corneum of the skin in a vicinity of the ablation electrodes, so as to facilitate transdermal transport of a substance.

12 Claims, 16 Drawing Sheets

U.S. PATENT DOCUMENTS

| | | |
|---|---|---|
| 5,281,825 A | 1/1994 | Berndt et al. |
| 5,318,514 A | 6/1994 | Hofmann |
| 5,328,478 A | 7/1994 | McVay |
| 5,380,272 A | 1/1995 | Gross |
| 5,409,835 A | 4/1995 | Lakowicz et al. |
| 5,421,817 A | 6/1995 | Liss et al. |
| 5,423,803 A | 6/1995 | Tankovich et al. |
| 5,439,440 A | 8/1995 | Hofmann |
| 5,445,609 A | 8/1995 | Lattin et al. |
| 5,445,611 A | 8/1995 | Eppstein et al. |
| 5,458,140 A | 10/1995 | Eppstein et al. |
| 5,462,520 A | 10/1995 | Hofmann |
| 5,464,386 A | 11/1995 | Hofmann |
| 5,485,530 A | 1/1996 | Lakowicz et al. |
| 5,500,437 A | 3/1996 | Saitoh et al. |
| 5,571,149 A | 11/1996 | Liss et al. |
| 5,582,168 A | 12/1996 | Samuels et al. |
| 5,624,847 A | 4/1997 | Lakowicz et al. |
| 5,628,310 A | 5/1997 | Rao et al. |
| 5,631,169 A | 5/1997 | Lakowicz et al. |
| 5,648,269 A | 7/1997 | Lakowicz et al. |
| 5,660,997 A | 8/1997 | Spaulding |
| 5,666,543 A | 9/1997 | Gartland |
| 5,674,267 A | 10/1997 | Mir et al. |
| 5,681,282 A | 10/1997 | Eggers et al. |
| 5,688,232 A | 11/1997 | Flower |
| 5,697,896 A | 12/1997 | McNichols et al. |
| 5,698,217 A | 12/1997 | Wilking |
| 5,720,772 A | 2/1998 | Eckhouse |
| 5,722,397 A | 3/1998 | Eppstein |
| 5,759,767 A | 6/1998 | Lakowicz et al. |
| 5,792,049 A | 8/1998 | Eppstein et al. |
| 5,860,421 A | 1/1999 | Eppstein et al. |
| 5,871,469 A | 2/1999 | Eggers et al. |
| 5,885,211 A | 3/1999 | Eppstein et al. |
| 5,902,272 A | 5/1999 | Eggers et al. |
| 5,911,223 A | 6/1999 | Weaver et al. |
| 5,924,981 A | 7/1999 | Rothfritz et al. |
| 5,938,657 A | 8/1999 | Assa et al. |
| 5,964,726 A | 10/1999 | Korenstein et al. |
| 5,983,130 A | 11/1999 | Phipps et al. |
| 5,983,131 A | 11/1999 | Weaver et al. |
| 5,983,135 A | 11/1999 | Avrahami |
| 6,002,482 A | 12/1999 | Rothfritz et al. |
| 6,009,344 A | 12/1999 | Flower et al. |
| 6,022,316 A | 2/2000 | Eppstein et al. |
| 6,024,733 A | 2/2000 | Eggers et al. |
| 6,030,399 A | 2/2000 | Ignotz et al. |
| 6,041,253 A | 3/2000 | Kost et al. |
| 6,045,502 A | 4/2000 | Eppstein et al. |
| 6,050,988 A | 4/2000 | Zuck |
| 6,055,451 A | 4/2000 | Bambot et al. |
| 6,066,134 A | 5/2000 | Eggers et al. |
| 6,076,012 A | 6/2000 | Swanson et al. |
| 6,083,196 A | 7/2000 | Trautman et al. |
| 6,088,606 A | 7/2000 | Ignotz et al. |
| 6,090,106 A | 7/2000 | Goble et al. |
| 6,104,952 A | 8/2000 | Tu et al. |
| 6,117,109 A | 9/2000 | Eggers et al. |
| 6,142,922 A | 11/2000 | Yoshikawa et al. |
| 6,142,939 A | 11/2000 | Eppstein et al. |
| 6,148,232 A | 11/2000 | Avrahami |
| 6,159,194 A | 12/2000 | Eggers et al. |
| 6,169,224 B1 | 1/2001 | Heinecke et al. |
| 6,173,202 B1 | 1/2001 | Eppstein |
| 6,183,434 B1 | 2/2001 | Eppstein |
| 6,192,734 B1 | 2/2001 | Rothfritz et al. |
| 6,210,402 B1 | 4/2001 | Olsen et al. |
| 6,228,078 B1 | 5/2001 | Eggers et al. |
| 6,235,020 B1 | 5/2001 | Cheng et al. |
| 6,238,391 B1 | 5/2001 | Olsen et al. |
| 6,339,775 B1 | 1/2002 | Zamanian et al. |
| 6,352,506 B1 | 3/2002 | Eppstein et al. |
| 6,508,785 B1 | 1/2003 | Eppstein |
| 6,512,950 B2 | 1/2003 | Li et al. |
| 6,527,716 B1 | 3/2003 | Eppstein |
| 6,530,915 B1 | 3/2003 | Eppstein et al. |
| 6,597,946 B2 | 7/2003 | Avrahami et al. |
| 6,603,998 B1 | 8/2003 | King et al. |
| 6,611,706 B2 | 8/2003 | Avrahami et al. |
| 6,611,707 B1 | 8/2003 | Prausnitz et al. |
| 6,692,456 B1 | 2/2004 | Eppstein et al. |
| 6,708,060 B1 | 3/2004 | Avrahami et al. |
| 6,711,435 B2 | 3/2004 | Avrahami |
| 6,713,291 B2 | 3/2004 | King et al. |
| 7,062,317 B2 | 6/2006 | Avrahami et al. |
| 7,123,957 B2 | 10/2006 | Avrahami |
| 7,164,942 B2 | 1/2007 | Avrahami et al. |
| 7,335,377 B2 | 2/2008 | Stern et al. |
| 7,363,075 B2 | 4/2008 | Stern et al. |
| 7,383,084 B2 | 6/2008 | Stern et al. |
| 7,395,111 B2 | 7/2008 | Levin et al. |
| 7,415,306 B2 | 8/2008 | Levin et al. |
| 7,558,625 B2 | 7/2009 | Levin et al. |
| 2001/0051180 A1 | 12/2001 | Watanabe et al. |
| 2002/0010412 A1 | 1/2002 | Eppstein |
| 2002/0010414 A1* | 1/2002 | Coston et al. ............ 604/20 |
| 2002/0091311 A1 | 7/2002 | Eppstein et al. |
| 2002/0099308 A1 | 7/2002 | Bojan et al. |
| 2002/0169394 A1 | 11/2002 | Eppstein et al. |
| 2003/0078499 A1 | 4/2003 | Eppstein |
| 2003/0092982 A1 | 5/2003 | Eppstein |
| 2004/0039342 A1 | 2/2004 | Eppstein et al. |
| 2004/0039343 A1 | 2/2004 | Eppstein et al. |
| 2005/0119605 A1 | 6/2005 | Sohn |
| 2007/0031495 A1 | 2/2007 | Eppstein et al. |
| 2007/0270732 A1 | 11/2007 | Levin et al. |
| 2007/0287949 A1 | 12/2007 | Levin et al. |
| 2007/0292445 A1 | 12/2007 | Levin |
| 2008/0114281 A1 | 5/2008 | Birchall et al. |
| 2008/0208107 A1 | 8/2008 | McRae et al. |
| 2008/0274166 A1 | 11/2008 | Sacks et al. |
| 2009/0264810 A1 | 10/2009 | Eppstein et al. |
| 2010/0174224 A1 | 7/2010 | Sohn |
| 2010/0293807 A1 | 11/2010 | Bar-El et al. |

FOREIGN PATENT DOCUMENTS

| | | |
|---|---|---|
| JP | 06007457 | 1/1994 |
| WO | WO9310854 A1 | 6/1993 |
| WO | WO9414062 A1 | 6/1994 |
| WO | WO9416765 A1 | 8/1994 |
| WO | WO9427671 A1 | 12/1994 |
| WO | WO96/22808 A1 | 1/1996 |
| WO | WO9617651 A1 | 6/1996 |
| WO | WO9640364 A1 | 12/1996 |
| WO | WO9707734 A1 | 3/1997 |
| WO | WO9716222 A1 | 5/1997 |
| WO | WO9800193 A1 | 1/1998 |
| WO | WO9829134 A2 | 7/1998 |
| WO | WO9944507 A1 | 9/1999 |
| WO | WO9944508 A1 | 9/1999 |
| WO | WO9944637 A1 | 9/1999 |
| WO | WO9944638 A1 | 9/1999 |
| WO | WO9944678 A1 | 9/1999 |
| WO | WO0003758 A1 | 1/2000 |
| WO | WO0004832 A1 | 2/2000 |
| WO | WO0015102 A1 | 3/2000 |
| WO | WO0044438 A1 | 8/2000 |
| WO | WO0059371 A1 | 10/2000 |
| WO | WO0074583 A1 | 12/2000 |
| WO | WO0074763 A2 | 12/2000 |
| WO | WO0074767 A2 | 12/2000 |
| WO | WO0076575 A2 | 12/2000 |
| WO | WO0113989 A1 | 3/2001 |
| WO | WO0135820 A1 | 5/2001 |
| WO | WO02090210 A1 | 11/2002 |
| WO | WO03039620 A2 | 5/2003 |
| WO | WO03077971 A3 | 12/2003 |
| WO | WO03077970 A3 | 2/2004 |
| WO | WO03101507 A3 | 3/2004 |
| WO | WO2006131931 A3 | 1/2007 |
| WO | WO2008091878 A1 | 7/2008 |
| WO | WO2009047774 A2 | 4/2009 |

OTHER PUBLICATIONS

European Search Report dated Apr. 7, 2011, which issued during the prosecution of Applicant's EP 11 00 0062.

An Examination Report dated Apr. 6, 2011, which issued during the prosecution of Applicant's EP 99952784.9.

International Searach Report dated Dec. 8, 2006 for PCT Patent Application PCT/IL2006/00679.

Henry, S. et al., "Micromachined Needles for the Transfermal Delivery of Drugs", IEEE 11th Annual International Workshop on Micro-Electric-Mechanical Systems, 1998, pp. 494-498.

Chizmadzhev, Yuri A., et al., "Electrical Properties of Skin at Moderate Voltages: Contribution of Appendageal Macropores", Biophysical Journal, Feb. 1998, vol. 74, pp. 843-856.

"Instructions Manual for the Force 2 Electrosurgical Generator", Valleylab/TycoHealthcare Group LP, Boulder, Colorado 1999.

U.S. Appl. No. 60/374,224, "Rotary handled transdermal drug delivery and analyte extraction", filed Apr. 19, 2002.

An office action dated Sep. 8, 2010, which issued during the prosecution of Applicant's European Patent Application No. 99 952 784.9.

An office action dated Sep. 2, 2010, which issued during the prosecution of Applicant's Japanese Patent Application No. 2000-580699.

An office action dated Sep. 30, 2010, which issued during the prosecution of Applicant's U.S. Appl. No. 12/721,030.

An office action dated Feb. 22, 2007, which issued during the prosecution of Applicant's European Patent Application No. EP 02730666.1.

* cited by examiner

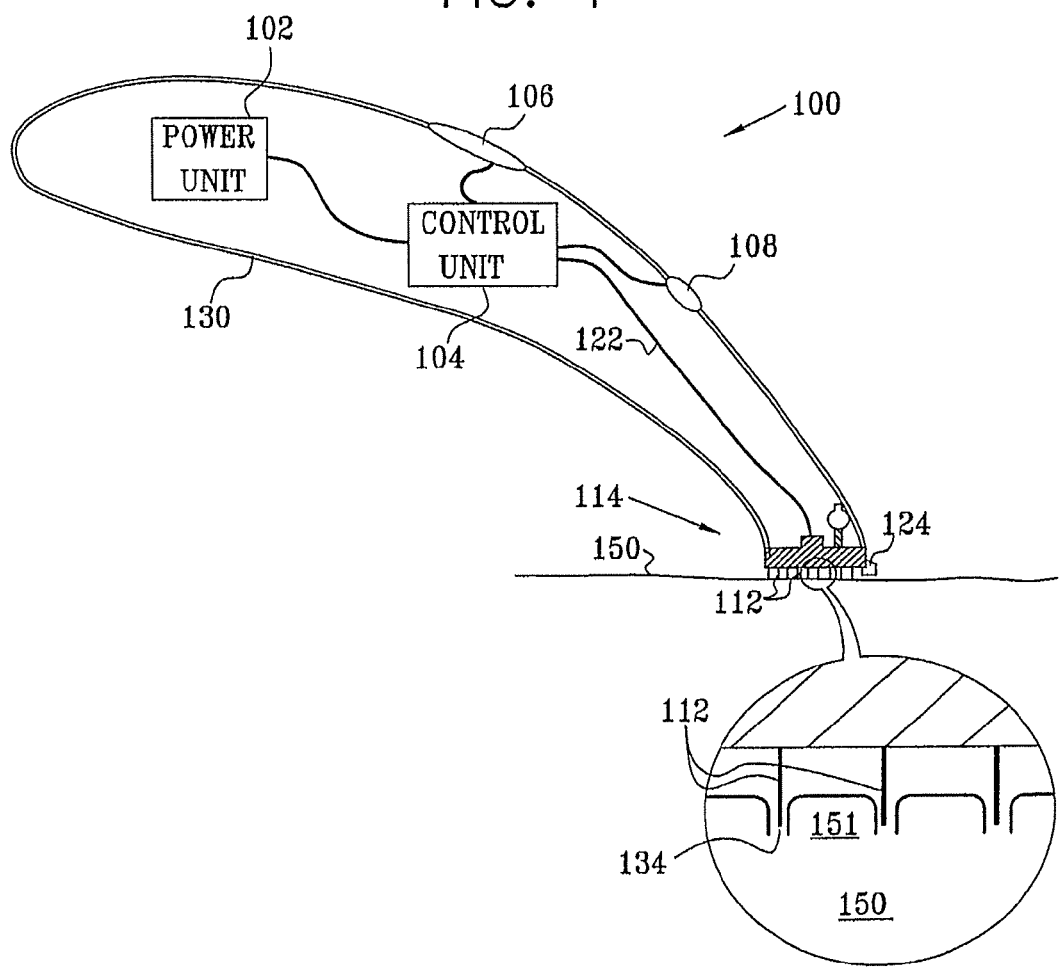

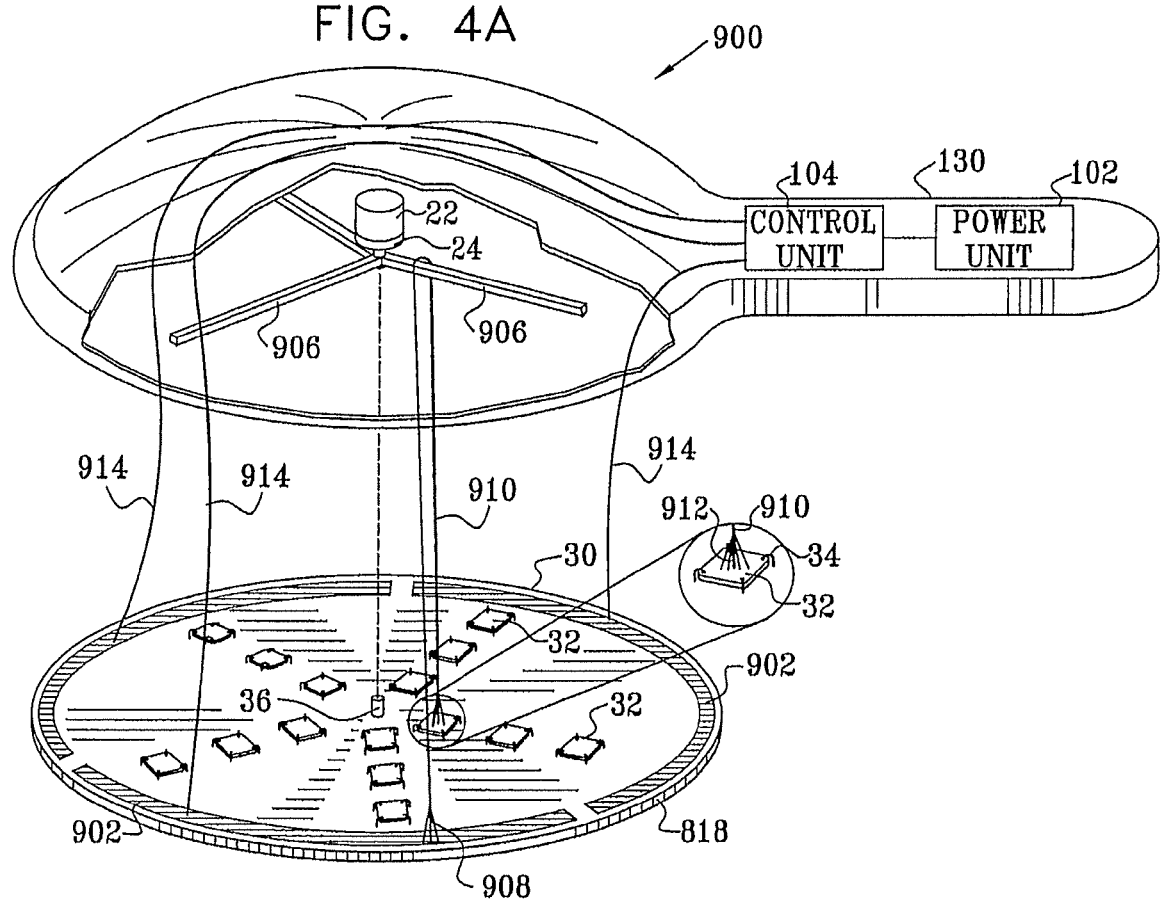

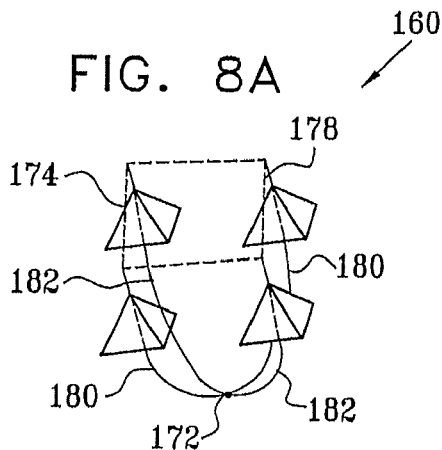
FIG. 8A
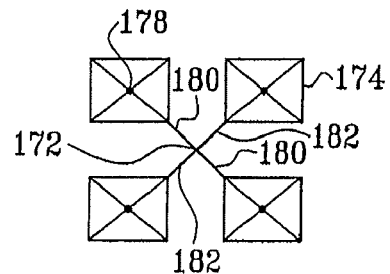
FIG. 8B
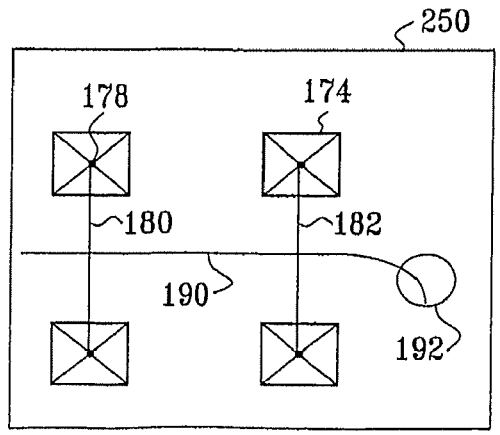
FIG. 8C
FIG. 8D

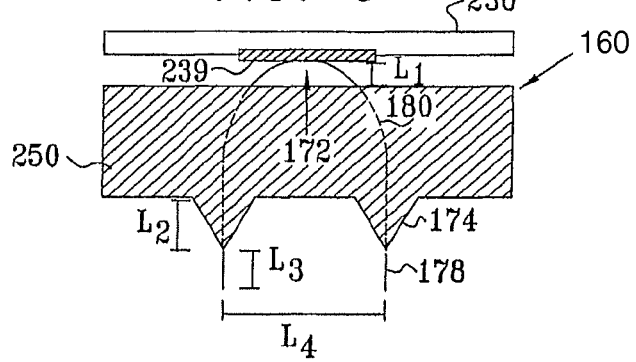
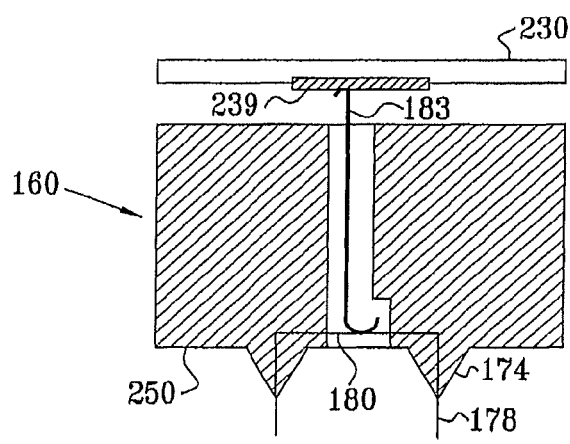
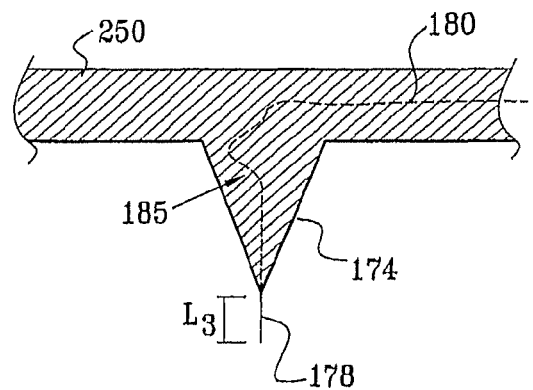

| | COLUMNS | | | |
|---|---|---|---|---|
| | A | B | C | D |
| 1 | 16 | 13 | 11 | 1,17 |
| 2 | 3 | 6 | 8 | 14 |
| 3 | 12 | 10 | 2,18 | 5 |
| 4 | 7 | 4 | 15 | 9 |

HANDHELD TRANSDERMAL DRUG DELIVERY AND ANALYTE EXTRACTION

CROSS-REFERENCE TO RELATED APPLICATION

This application is a continuation of U.S. application Ser. No. 10/511,966, which is the US National Phase of International Patent Application PCT/IL03/00314, filed Apr. 15, 2003, entitled, "Handheld transdermal drug delivery and analyte extraction," and published in English as WO03/089043 on Oct. 30, 2003, which claims priority from U.S. Provisional Patent Application 60/374,224, filed Apr. 19, 2002, entitled, "Rotary handheld transdermal drug delivery and analyte extraction," which is assigned to the assignee of the present patent application and incorporated herein by reference.

FIELD OF THE INVENTION

The present invention relates generally to methods and devices for drug delivery and analyte extraction, and specifically to medical methods and devices for puncturing the outer layer of living skin and to methods and devices for transdermal transport of a substance.

BACKGROUND OF THE INVENTION

A number of different methods have been developed to perform transdermal drug delivery and/or analyte extraction, including passive diffusion of a drug or analyte between a skin patch and skin, as well as active processes such as iontophoresis, sonophoresis, electroporation, and chemically enhanced diffusion. These methods are primarily used for generating transdermal movement of small molecules, but generally do not enhance the motion of large molecules through the 10-50 micron thick outermost layer of the skin, the stratum corneum epidermidis.

PCT Publication WO 97/07734 describes thermal ablation of the stratum corneum using an electrically resistive element in contact with the stratum corneum, such that a high current through the element causes a general heating of tissue in its vicinity, most particularly the stratum corneum.

U.S. Pat. No. 5,019,034 to Weaver et al., whose disclosure is incorporated herein by reference, describes apparatus for applying high voltage, short duration electrical pulses on the skin to produce electroporation, and states that "... reversible electrical breakdown ... along with an enhanced tissue permeability, is the characteristic effect of electroporation."

U.S. Pat. Nos. 5,885,211, 6,022,316, 6,142,939 and 6,173,202 to Eppstein et al., which are incorporated herein by reference, describe methods for forming micropores in the stratum corneum by heating tissue-bound water above the vapor point with a heat conducting element, so as to enhance transdermal transport of an analyte or active substance. Further enhancement techniques include the use of sonic energy, pressure, and chemical enhancers.

U.S. Pat. No. 5,688,233 to Hofmann et al., which is incorporated herein by reference, describes a method of transdermal molecular delivery including providing molecules to be delivered mixed with particles, contacting a selected area of a skin surface with the particles and molecules, applying a pulsed electric field of sufficient amplitude and duration to induce dielectric breakdown of the stratum corneum, and applying a pressure to the molecules to force transport of the molecules through the pores in the stratum corneum into the underlying skin.

U.S. Pat. No. 5,318,514 to Hofmann, which is incorporated herein by reference, describes an apparatus for implanting macromolecules such as genes, DNA or pharmaceuticals into a preselected surface tissue region of a patient. An applicator having a plurality of electrodes is provided for contacting a surface tissue region of a patient. A mechanism associated with the applicator delivers a predetermined quantity of a fluid medium carrying the preselected macromolecules. A signal generator is provided for generating a predetermined electric signal. The electrodes of the applicator are connected to the signal generator for applying an electric field in the surface tissue region. The field has a predetermined strength and duration in order to make the walls of a plurality of cells in the surface tissue region transiently permeable to permit the macromolecules to enter said preselected cells without damaging said cells. This technique is described as enhancing the uptake of macromolecules and thus enhancing the therapeutic effect achieved.

U.S. Pat. No. 5,462,520 to Hofmann, which is incorporated herein by reference, describes a method of transtissue molecular delivery that includes encapsulating molecules to be delivered in a microbubble carrier, contacting a selected area of a tissue surface with a solution of the encapsulated molecules, and applying an electric field of sufficient amplitude to induce electrofusion between the tissue and the membrane of the microbubble.

U.S. Pat. No. 5,464,386 to Hofmann, which is incorporated herein by reference, describes a method of transdermal molecular delivery that includes encapsulating molecules to be delivered in a vesicle, contacting a selected area of a tissue surface with a solution of the vesicles, and applying a pulsed electric field of sufficient amplitude to induce dielectric breakdown of the stratum corneum and to induce transport of the intact vesicle through the pores in the stratum corneum into the underlying tissue to enable diffusion of molecules into the tissue.

U.S. Pat. No. 3,964,482 to Gerstel, U.S. Pat. No. 6,050,988 to Zuck, and U.S. Pat. No. 6,083,196 to Trautman et al., which are incorporated herein by reference, describe other apparatus and methods for facilitating transdermal movement of a substance.

U.S. Pat. No. 6,148,232 to Avrahami, which is assigned to the assignee of the present patent application and is incorporated herein by reference, describes apparatus for applying electrodes at respective points on skin of a subject and applying electrical energy between two or more of the electrodes to cause cell heating and subsequent ablation of the stratum corneum primarily in areas near the respective points. Various techniques for limiting ablation primarily to the stratum corneum are described, including spacing of the electrodes and monitoring the electrical resistance of skin between adjacent electrodes.

Electrosurgery is commonly used during surgical procedures today, particularly in endoscopic and laparoscopic surgery where direct access to the tissue being dissected is limited. Electrosurgery involves applying radio frequency electric current to electrodes which are used to sever tissue or achieve homeostasis. A publication entitled "Instruction Manual for the Force 2 Electrosurgical Generator" (Valleylab/Tyco Healthcare Group LP, Boulder, Colo.), which is incorporated herein by reference, describes the modes of operation of electrosurgical devices.

U.S. Pat. No. 6,159,194 to Eggers et al., which is incorporated herein by reference, describes electrosurgical apparatus and methods for inducing tissue contraction, without ablation or dissociation of surrounding tissue, in order to reduce wrinkles in skin.

U.S. Pat. Nos. 6,066,134 and 6,024,733 to Eggers et al., which are incorporated herein by reference, describe electrosurgical apparatus and methods for ablating outer layers of skin for the treatment of unwanted tissue pigmentations, melanomas, and other skin disorders.

U.S. Pat. No. 6,090,106 to Goble et al., which is incorporated herein by reference, describes monopolar and bipolar electrosurgical instruments for ablating gross tissue, such as the prostate or endometrial tissue.

U.S. Pat. No. 4,943,290 to Rexroth et al., which is incorporated herein by reference, describes electrosurgical apparatus in which a nonconductive fluid is transported to the region of an electrode in order to isolate the electrode and prevent undesirable damage of surrounding tissue.

PCT Publication WO 02/085451 to Avrahami et al., and the corresponding U.S. patent application Ser. No. 09/840,522, which are incorporated herein by reference, describe a skin treatment device that includes a plurality of electrodes, which are adapted to be placed in contact with the skin and then moved across the skin while maintaining electrical contact with the skin. The device additionally includes a power source, which is adapted to apply a current between two or more of the plurality of electrodes at the same time as the electrodes are being moved across the skin.

PCT Publication WO 02/091934 to Avrahami et al., and the corresponding U.S. patent application Ser. No. 09/859,645, which are incorporated herein by reference, describe a device for facilitating transdermal passage of a substance through skin on the body of a subject. The device preferably includes an electrode and a control unit. In a preferred embodiment, the control unit is adapted to drive the electrode to apply to the skin a current capable of ablating stratum corneum epidermidis of the skin, so as to facilitate transdermal passage of the substance. The control unit detects generation of at least one spark responsive to application of the current, and modifies a parameter of the current responsive to detecting the generation of the at least one spark.

SUMMARY OF THE INVENTION

In some preferred embodiments of the present invention, a handheld device for facilitating transdermal transport of a substance, such as a drug, comprises (a) a plurality of ablation electrodes, which are to be placed in contact with skin of a subject, (b) a plurality of electrically-conductive contact pads, each contact pad electrically coupled to one or more of the ablation electrodes, (c) one or more driving electrodes, (c) a handle, and (d) a control unit, adapted to apply current to the driving electrodes, and to rotate the driving electrodes so as to cause them to intermittently come in contact with each contact pad, thereby causing the ablation electrodes coupled to that contact pad to drive the current into the skin. As a result, at least one micro-channel is created in the stratum corneum of the skin, enabling or augmenting transdermal transport of the substance. Preferably, the handheld device comprises a motor for rotating the driving electrodes, and the driving electrodes comprise brush electrodes.

In some preferred embodiments of the present invention, the handheld device comprises an electrode board, which is mechanically and preferably removably coupled to the handle. The upper surface of the electrode board comprises the contact pads, and the lower surface of the electrode board comprises the ablation electrodes. Preferably, but not necessarily, each contact pad is electrically coupled to a plurality (e.g., four) of the ablation electrodes. The electrode board is typically discarded after a single use.

In other preferred embodiments of the present invention, the handheld device comprises a contact board, which is mechanically coupled to the handle. The lower surface of the contact board comprises contact board contacts, and the upper surface of the contact board comprises the contact pads, each of which is electrically coupled to at least one of the contact board contacts. The handheld device further comprises an electrode cartridge, which is removably coupled to the handheld device. The lower surface of the electrode cartridge comprises a plurality of ablation electrodes, which are held in a vicinity of the skin of the subject. The upper surface of the electrode cartridge comprises cartridge contacts, each of which is electrically coupled to at least one of the ablation electrodes, preferably to a plurality (e.g., 2-10) of the ablation electrodes. When the electrode cartridge is coupled to the handheld device, the cartridge contacts make electrical contact with the contact board contacts. As a result, when a driving electrode makes contact with a contact pad, a current is driven (a) from the driving electrode, (b) to the contact pad, (c) to at least one contact board contact, (d) to at least one cartridge contact, (e) to at least one ablation electrode, and (f) into the skin of the subject. Preferably, the electrode cartridge is discarded after a single use.

In some preferred embodiments of the present invention, the handheld device comprises a rotation assembly, which comprises a rotational energy applicator, such as a motor or a manual crank. For some applications, the rotation assembly comprises a support element, such as a manifold, comprising the driving electrodes. Alternatively, the rotation assembly comprises a rotating disk that is driven by a driving gear, the disk comprising the driving electrodes and being configured such that the driving electrodes are arranged in one or more generally radial lines on the disk. Preferably, the rotation assembly comprises a position sensor, which monitors the motion of the support element or the rotating disk, as the case may be, so as to facilitate the controlled ablation by some or all of the ablation electrodes of stratum corneum in contact therewith.

In some preferred embodiments of the present invention, the electrode board or contact board, as the case may be, comprises a printed circuit board (PCB), preferably a multi-layered PCB. Contact pads on the upper surface of the PCB are electrically coupled to at least one contact board contact or ablation electrode, as the case may be, over one or more traces, as is known in the art of PCB design and fabrication. The use of a PCB, particularly a multi-layered PCB, allows contact board contacts or ablation electrodes, as the case may be, to be readily placed at locations other than in the vicinity of the respective contact pads to which they are electrically coupled.

In some preferred embodiments of the present invention, the handheld device comprises a plurality of power tracks, e.g., three, on the electrode board or contact board, as the case may be, preferably corresponding to the number of contact pads in each line extending radially from the center of the electrode board or contact board. The power tracks are coupled by power transfer elements to the contact pads. A first end of each power transfer element comprises a track contact, which comes in electrical contact with the power tracks as the power transfer element rotates. A second end of each power transfer element comprises a driving electrode, which comes in electrical contact with at least a portion of the contact pads as the power transfer element rotates. For some applications, each power transfer element is a shaped piece of metal, one end of which (defining the track contact) is brought into electrical contact with the power track, and the other end of which (defining the driving electrode) is brought into electrical contact with the contact pads. Typically, but not necessarily, only one power transfer element is in contact with a given power track at any time, and the control unit only applies power to one power track at a time.

In some embodiments of the present invention, the PCB comprises at least two non-conducting layers, an upper non-conducting layer and a lower non-conducting layer, which are separated by a conducting layer. Contact pads on the upper non-conducting layer are electrically coupled to electrodes or contact board contacts mounted on the skin-facing side of the lower non-conducting layer. The conducting layer serves as a ground, by virtue of being electrically coupled to a negative terminal of the power unit. A capacitive element is naturally formed by the lower non-conducting layer separating the conducting layer and the contact board contacts or electrodes. Therefore, handheld devices that comprise this PCB assembly preferably do not comprise a return electrode, in contact with the skin, that is specifically designated to function as a ground. Instead, all of the ablation electrodes or contact board contacts, as the case may be, preferably "see" a small capacitance to ground, such that current injected through one of the ablation electrodes or contact board contacts sees a relatively-low resistance to ground via the capacitive coupling to ground provided by the other electrodes in this configuration.

In some preferred embodiments of the present invention, the handheld devices comprise electrode sets comprising at least two wires, which are bent and crossed with one another at about the middle of each wire, such that the ends of the wires substantially form a plane. Preferably, cone- or pyramid-style pieces (or pieces having other shapes) surround and support the ends of the wires, a portion of which protrude from the pieces and function as the ablation electrodes. The point defined by the intersection of the wires of the electrode set is brought in electrical contact with a contact board contact. Alternatively, a coupling member, electrically coupled to and in contact with the intersection point, is brought in electrical contact with a contact board contact. Preferably, the wires of the electrode set are shaped so as to define an angular bend, such as a crimp or a 90 degree bend, as they pass through the cone- or pyramid-style piece, in order to enhance the friction effect holding the wires in place in the pieces. Typically, the wires have a diameter less than about 150 microns.

In some preferred embodiments, electrodes are activated in an activation sequence pursuant to which the distances between each activated electrode and the successively activated electrode are generally greater than such distances would be pursuant to a random activation sequence. Larger distances between successively-activated electrodes generally minimizes any sensation of pain or discomfort that a subject might experience during ablation. For some applications, an activation sequence is generated by dividing an area including ablation electrodes into regions, such as rectangular regions, arranged in a grid, each region containing a plurality of electrodes. A sequence of regions is determined such that sequential regions are at least a minimum threshold distance apart. During ablation, the device cycles through the regions, so that sequentially-activated regions are generally at least a minimum threshold distance apart, and activates an electrode in each region. The sequence is typically cycled through at least twice, with a different electrode in each region preferably activated each time the sequence is repeated. Since sequential regions are at least the minimum threshold distance apart, each electrode within a region is at least the minimum threshold distance apart from the electrode activated in the next region in the sequence. Therefore, the sequence of activating electrodes within a given region during successive cycles of the sequence is generally not important, which affords flexibility in designing a contact board. In a preferred embodiment, sequential regions are at least the distance of a "knight's jump" (as in a game of chess) from one another, or are separated by at least one intervening region. The sequence is preferably configured to attempt to maximize both the average distance between sequentially activated electrodes and the minimum distance between sequentially activated electrodes.

When forming micro-channels in the stratum corneum, it is generally desirable to apply the minimum energy necessary to successfully form the micro-channels. Minimizing the applied energy reduces device energy requirements, which is particularly beneficial for battery-operated devices. Applying less energy may also reduce any sensation a subject might feel during ablation. While an appropriate voltage to apply can be pre-configured in an ablation device, it is desirable in some applications to calibrate the applied voltage at least once per use of the device. Such repeated calibration is beneficial because the impedance of stratum corneum varies from subject to subject, and even from time to time within a given subject (for example, because of varying moisture levels of the stratum corneum). Furthermore, for some applications, it is desirable to separately calibrate the applied voltage for many of the ablation electrodes or for each ablation electrode in an array of electrodes, because the impedance of stratum corneum sometimes varies even over a small area of skin.

In some preferred embodiments of the present invention, this calibration is performed using a technique of "feed-forward," as follows. A set of ablation electrodes is applied to the skin of the subject. Using at least one ablation electrode, a brief calibration burst of energy is applied to the stratum corneum. The calibration burst is applied at a relatively low energy level (e.g., a low voltage or a low current), such that ablation substantially does not occur, and no sensation is typically felt by the subject. A parameter of the calibration burst (e.g., current or voltage), generally indicative of a level of impedance in the stratum corneum, is measured. Responsive to the measured parameter, an appropriate energy level, such as a voltage or a current, to use for subsequent ablation is determined. Ablation is then performed using this energy level.

In some preferred embodiments, the handheld devices described herein comprise a pressure-sensing mechanism, adapted to provide an indication that firm contact has been made between an electrode cartridge and skin of the subject, responsive to which indication an ablation procedure is begun. The pressure-sensing mechanism preferably comprises a floating element, coupled to the handle of the handheld device by a pivot joint, which allows the floating element to pivot. A contact board is fixed to the lower surface of the floating element. The electrode cartridge is removably coupled to the contact board using snaps, which are adapted to prevent the electrode cartridge from separating from the contact board (as would otherwise typically occur because of gravity), while generally not applying any upward pressure on the electrode cartridge. A spring coupled to the handle applies downward pressure on the floating element. When the electrode cartridge is brought in contact with the skin, and downward pressure is applied using the handle, the floating element is pushed upward, activating a switch on the floating element, thereby indicating that firm contact has been made between the electrode cartridge and the skin. Alternatively, the pressure-sensing mechanism comprises a force-detecting spring, such as a force transducer, instead of lower and upper contacts.

In some preferred embodiments of the present invention, packaging is provided for storing an electrode-containing element, such as an electrode cartridge or an electrode board. The packaging comprises a container, preferably comprising blister packaging, as is known in the art. The container is typically shaped so as to define an indentation, adapted to store the electrode-containing element. To close the packaging and maintain cleanliness of the electrode-containing element prior to use, the container is covered with a removable covering. The indentation is positioned so that, when the electrode-containing element is seated in the indentation, the plane formed by the electrodes of the electrode-containing element and the plane formed by the covering form an angle of between 5 and 90 degrees, preferably between about 10 and 35 degrees. The angle is preferably configured to facilitate easy grasping of the handle by a user while using the handle to remove the electrode-containing element.

In order to attach the electrode-containing element to the handle of the handheld device (or contact board of the handheld device, as the case may be), the covering is removed by the user. The handle is inserted into an open area of the packaging and brought in contact with the top of the electrode-containing element. Pressure is preferably applied, which couples the handle to the electrode-containing element. The handle is then removed from the packaging.

In some preferred embodiments of the present invention, a patch, which is to be placed on the skin, comprises a plurality of ablation electrodes and, optionally, at least one return electrode. A handheld unit comprises a control unit coupled to provide power to at least one driving electrode, which, in turn, is adapted to drive one or more of the ablation electrodes upon electrical contact therewith, as the handheld unit is moved over the patch. Preferably, at any given time, only one of the driving electrodes is activated as the handheld unit is passed over the patch, so only some of the ablation electrodes are activated in a given pass. Thus, multiple passes of the handheld unit are typically utilized in order to activate all of the ablation electrodes. In this manner, the instantaneous power requirements of the device are reduced, and sensations felt by the patient are minimized during treatment.

In other preferred embodiments, the handheld unit comprises a driving mechanism such as a belt, which is disposed around two cylinders. The handheld unit further comprises a motor, coupled to one of the cylinders, and adapted to rotate the cylinder so as to cause movement of the belt and of the driving electrodes. As the driving electrodes pass over the patch, the driving electrodes make electrical contact with a portion of the ablation electrodes. For some applications, only some of the ablation electrodes are activated in a single pass of the driving electrodes, such that multiple passes of the driving electrodes are utilized in order to activate the ablation electrodes.

Some embodiments of the present invention incorporate methods and apparatus described in U.S. patent application Ser. No. 09/859,645 to Avrahami and Sohn, filed May 17, 2001, entitled, "Monopolar and bipolar current application for transdermal drug delivery and analyte extraction," which is assigned to the assignee of the present patent application and incorporated herein by reference. For example, the '645 application describes maintaining the ablation electrodes either in contact with the skin, or up to a distance of about 500 microns therefrom. The '645 application further describes ablation of the stratum corneum by applying a field having a frequency between about 10 kHz and 4000 kHz, preferably between about 10 kHz and 500 kHz.

Alternatively or additionally, preferred embodiments of the present invention incorporate methods and apparatus described in U.S. patent application Ser. No. 09/840,522 to Avrahami and Sohn, filed Apr. 23, 2001, entitled, "Handheld apparatus and method for transdermal drug delivery and analyte extraction," which is assigned to the assignee of the present patent application and incorporated herein by reference. Still further alternatively or additionally, preferred embodiments of the present invention incorporate methods and apparatus described in the above-cited U.S. Pat. No. 6,148,232 to Avrahami.

The term "micro-channel" as used in the context of the present patent application refers to a pathway generally extending from the surface of the skin through all or a significant part of the stratum corneum, through which pathway molecules can diffuse. Preferably, micro-channels allow the diffusion therethrough of large molecules at a greater rate than the same molecules would diffuse through pores generated by electroporation. Micro-channels are typically about 30-150 microns in diameter, and typically extend about 20-200 microns into the skin.

In some preferred embodiments of the present invention, ablation is performed using an array of electrodes, preferably closely-spaced electrodes, which act together to produce a high micro-channel density in an area of the skin under the cartridge. Typically, however, the overall area of micro-channels generated in the stratum corneum is small compared to the total area covered by the electrode array.

For some applications, a user applies the device to himself, in which case the "user" and the "subject," as used herein, are the same person.

In some embodiments of the present invention, one or more of the ablation electrodes serve as return electrodes. Preferably, these return ablation electrodes collectively have a relatively large contact surface area with the skin, resulting in relatively low current densities in the skin near the return ablation electrodes, and thus no significant heating or substantial damage to the skin in this vicinity. In proximity to each ablation electrode in the electrode array, by contrast, the high current density of the applied field typically induces rapid heating and ablation of the stratum corneum.

In some preferred embodiments of the present invention, the handheld device comprises an output unit coupled to the control unit, to enable the control unit to communicate pertinent information to the user. Preferably, the information comprises some or all of the following:

the operational status of the device,
an indication following successful ablation of the stratum corneum by the ablation electrodes,
the number of micro-channels formed in the current application of the device, and
the amount of skin surface treated by the device.

Preferably, the output unit comprises a display, such as an LCD or LED. Alternatively or additionally, the output unit comprises a speaker or buzzer, preferably enabled to convey some of the information.

In some preferred embodiments, the handheld device ablates the stratum corneum so as to prepare the skin for substance delivery or analyte extraction by a separate substance delivery unit or analyte extraction unit. For example, a standard skin patch containing a drug could be applied to the region of skin ablated by the handheld device. Because ablation of the stratum corneum as provided by these embodiments typically produces essentially no sensation, the handheld device preferably comprises means for demarcating the region of skin prepared by the device. The demarcation helps the user to place the drug delivery unit or analyte extraction unit on the treated region of skin. For example, the device may comprise an ink or dye reservoir and means for delivering the ink or dye to the surface of the skin region which was treated by the device. Alternatively or additionally, techniques are used that are described in PCT Patent Application PCT/IL02/00896 to Sohn, filed Nov. 7, 2002, entitled, "Integrated transdermal drug delivery system," which is assigned to the assignee of the present patent application and is incorporated herein by reference.

In other preferred embodiments, the handheld device is used both to prepare the skin for substance delivery and to deliver the substance to the surface of the prepared skin. Preferably, the handheld apparatus comprises a substance reservoir and means for delivering the substance to the surface of the skin. For example, a porous material may be placed between adjacent electrodes, and coupled to the substance reservoir by a conduit such that the substance can flow from the reservoir, through the porous material, to the skin.

There is therefore provided, in accordance with an embodiment of the present invention, apparatus for application to skin of a subject, including:

a board having a first surface and a second surface, the first surface including a plurality of ablation electrodes, which are adapted to be applied to the skin, and the second surface including one or more contact pads, each one of the contact pads electrically coupled to at least one of the ablation electrodes;

one or more driving electrodes;

an energy applicator, coupled to the driving electrodes, the energy applicator adapted to pass the driving electrodes over the contact pads;

a power source, adapted to drive a current
from the driving electrodes,
to the contact pads,
to the ablation electrodes, capable of ablating at least a portion of stratum corneum of the skin in a vicinity of the ablation electrodes, so as to facilitate transdermal transport of a substance.

In an embodiment, the energy applicator is adapted to pass the driving electrodes over the contact pads such that at any given time less than all of the driving electrodes are in electrical contact with one or more of the contact pads.

The power source is typically adapted to selectively drive the current to a subset of the driving electrodes.

For some applications, the energy applicator includes a motor or a manual crank.

The power source is typically adapted to drive the current such that skin layers beneath the stratum corneum are substantially not ablated.

For some applications, the apparatus includes a marking unit, adapted to apply a marking substance to the skin so as to demarcate a region of the skin to which the current is applied. Alternatively or additionally, the apparatus includes one or more protrusive elements, adapted to press the skin so as to demarcate a region of the skin to which the current is applied.

For some applications, at least one of the ablation electrodes is adapted to be applied to the skin so as to create a contact area having a characteristic length of between about 30 and 150 microns.

In an embodiment, the ablation electrodes include a current-driving ablation electrode and two or more return electrodes, and the power source is adapted to drive respective currents between the current-driving ablation electrode and each of the return electrodes.

For some applications, the plurality of ablation electrodes includes at least 100 ablation electrodes.

In an embodiment, the power source includes a first terminal and a second terminal, the first terminal adapted to be electrically coupled in sequence to at least a portion of the contact pads at least a portion of the time, and wherein the board includes:

a conductive element, adapted to be electrically coupled to the second terminal and substantially electrically isolated from the contact pads; and a dielectric having first and second dielectric surfaces thereof, the first dielectric surface adapted to be coupled to the conductive element and the second dielectric surface adapted to be coupled to the ablation electrodes, such that, during a given ablation application period, when the first terminal is in electrical contact with a first set including one or more of the contact pads, and the power source drives a current into the first set, a second set including one or more of the ablation electrodes, which are electrically isolated during the given ablation application period from all of the contact pads in the first set, function as a capacitive electrical return path for the current via the dielectric to the second terminal.

For some applications, the board includes a printed circuit board (PCB), and at least one of the ablation electrodes is coupled to the first surface at a point on the first surface that is at least 5 millimeters from at least one of the contact pads to which the at least one of the ablation electrodes is electrically coupled.

Alternatively or additionally, at least 25% of the ablation electrodes are coupled to the first surface at respective points on the first surface that are at least 3 millimeters from respective contact pads to which the ablation electrodes are electrically coupled.

The power source is typically adapted to drive the current so as to facilitate transport of the substance through the skin into a body of the subject. Alternatively or additionally, the power source is adapted to drive the current so as to facilitate transport of the substance through the skin from within a body of the subject.

In an embodiment, one or more of the contact pads are electrically coupled to respective pluralities of the ablation electrodes. In this case, one or more of the contact pads are typically electrically coupled to respective sets of at least four of the ablation electrodes.

For some applications, the contact pads are arranged in concentric circles on the second surface. In this case, the energy applicator may be adapted to rotate the driving electrodes over the contact pads.

In an embodiment, the apparatus includes a support element, supporting the driving electrodes, and the energy applicator is adapted to move the supporting element so as to pass the driving electrodes over the contact pads. In this case, the apparatus typically includes a position sensor, adapted to monitor a position of the support element, and the power source is adapted to regulate timing of the driving of the current responsive to the monitored position. Alternatively or additionally, the support element is adapted to be movably coupled to the board. In this case, the support element may be adapted to be rotatably coupled to the board, and the energy applicator may be adapted to rotate the support element so as to pass the driving electrodes over the contact pads. In an embodiment, the contact pads and the driving electrodes are adapted to be arranged such that each of the contact pads comes in contact with at least one of the driving electrodes during a rotation of the support element.

For some applications, the apparatus includes:

a plurality of power tracks, wherein the power source is adapted to supply power to the power tracks; and one or more power transfer elements, each having a first end and a second end, each of the power transfer elements including:

one of the driving electrodes, disposed at the first end of the power transfer element; and a track contact, disposed at the second end of the power transfer element, adapted to be in electrical contact with the one of the driving electrodes and to be brought into contact with at least one of the power tracks.

In an embodiment, each track contact is adapted to be brought into contact in sequence with at least two of the power tracks.

Typically, the power source is adapted to supply power, for ablating stratum corneum, to less than all of the power tracks at any given time.

In an embodiment, the power tracks are on the second surface of the board. Alternatively or additionally, the power tracks are disposed in concentric circles or has a shape of a partial arc.

For some applications, the power tracks are configured such that at any given time, each of the power tracks is in electrical contact with only one of the driving electrodes.

In an embodiment, the driving electrodes are configured such that at any given position of the driving electrodes, less than all of the driving electrodes are in electrical contact with a same one of the power tracks. In this case, the driving electrodes may be configured such that at a point in time during operation of the apparatus, a plurality of the driving electrodes are in electrical contact with different respective power tracks, and the power source may be adapted to drive the current into less than all of the plurality of the driving electrodes at the point in time.

There is also provided, in accordance with an embodiment of the present invention, apparatus for application to skin of a subject, including:

a contact board having a first contact board surface and a second contact board surface, the first contact board surface including one or more contact board contacts, and the second contact board surface including one or more contact pads, each contact pad electrically coupled to at least one of the contact board contacts;

an electrode cartridge removably coupled to the contact board, the electrode cartridge having a first cartridge surface and a second cartridge surface, the first cartridge surface including a plurality of ablation electrodes, which are adapted to be applied to the skin, and the second cartridge surface including one or more cartridge contacts, each cartridge contact electrically coupled to at least one of the ablation electrodes, such that when the electrode cartridge is coupled to the contact board, at least a portion of the contact board contacts come into electrical contact with at least a portion of the cartridge contacts;

one or more driving electrodes;

an energy applicator, coupled to the driving electrodes, the energy applicator adapted to pass the driving electrodes over the contact pads; and a power source, adapted to drive a current
from the driving electrodes,
to the contact pads,
to the contact board contacts,
to the cartridge contacts,
to the ablation electrodes,
capable of ablating at least a portion of stratum corneum of the skin in a vicinity of the ablation electrodes, so as to facilitate transdermal transport of a substance.

In an embodiment, the energy applicator is adapted to pass the driving electrodes over the contact pads such that at any given time less than all of the driving electrodes are in electrical contact with one or more of the contact pads.

Alternatively or additionally, the power source is adapted to selectively drive the current to a subset of the driving electrodes.

At least one of the ablation electrodes is typically adapted to be applied to the skin so as to create a contact area having a characteristic length of between about 10 and 100 microns.

In an embodiment, the electrode cartridge includes at least one housing and at least one set of two or more wires coupled to the housing, each wire having two ends and an intermediate portion, the wires supported by the housing, bent and crossed with one another at the intermediate portion of each wire, so that the intermediate portions of the wires touch each other and so that all of the ends of the wires substantially form a plane, the ends configured to function as at least four of the ablation electrodes.

In an embodiment, the intermediate portion of one of the wires is configured to function as one of the cartridge contacts and to be electrically coupled to one of the contact board contacts. For some applications, the apparatus includes a coupling member, adapted to electrically couple the intermediate portion of one of the wires to one of the contact board contacts.

In an embodiment, the set includes exactly two wires.

Each wire typically has a shape generally like a staple, but may have other shapes.

For some applications, each wire is adapted to be supported by the housing by passing through the housing, and a portion of each wire that passes through the housing is shaped so as to define an angular bend within the housing.

In an embodiment, the electrode cartridge includes:
at least one housing;
at least one set of two or more wires coupled to the housing, each wire having two ends and an intermediate portion, the wires supported by the housing so as not to touch each other; and
a coupling element, coupled to the intermediate portion of each of the wires, so that all of the ends of the wires substantially form a plane, the ends configured to function as at least four of the ablation electrodes.

In an embodiment, the coupling element is configured to function as one of the cartridge contacts and to be electrically coupled to one of the contact board contacts.

In an embodiment, the apparatus includes:
a plurality of power tracks, wherein the power source is adapted to supply power to the power tracks; and
one or more power transfer elements, each having a first end and a second end, each of the power transfer elements including:
one of the driving electrodes, disposed at the first end of the power transfer element; and
a track contact, disposed at the second end of the power transfer element, adapted to be in electrical contact with the one of the driving electrodes and to be brought into contact with at least one of the power tracks.

The power source is typically adapted to supply power, for ablating stratum corneum, to less than all of the power tracks at any given time. For some applications, the power tracks are on the contact board.

There is further provided, in accordance with an embodiment of the present invention, apparatus for application to skin of a subject, including:

a board, having a first surface and a second surface, the first surface including a plurality of conductors, adapted to be brought in contact with the skin, and the second surface including a plurality of contact pads, each of the contact pads electrically coupled to at least one of the conductors;

a power unit, having a first terminal and a second terminal, the first terminal adapted to be electrically coupled in sequence to at least a portion of the contact pads at least a portion of the time, the power unit adapted to drive a current from the contact pads to the conductors, capable of ablating stratum corneum of the skin in a vicinity of the conductors, so as to facilitate transdermal transport of a substance;

a conductive element, adapted to be electrically coupled to the second terminal and substantially electrically isolated from the contact pads; and a dielectric having first and second dielectric surfaces thereof, the first dielectric surface adapted to be coupled to the conductive element and the second dielectric surface adapted to be coupled to the conductors, such that, during a given ablation application period, when the first terminal is in electrical contact with a first set including one or more of the contact pads, and the power unit drives a current into the first set, a second set including one or more of the conductors, which are electrically isolated during the given ablation application period from all of the contact pads in the first set, function as a capacitive electrical return path for the current via the dielectric to the second terminal.

The apparatus is typically arranged to produce an impedance of the capacitive return path that is less than 5 kilo-ohms.

During any given ablation application period, the first set typically includes exactly one contact pad.

During any given ablation application period, a ratio of a number of contact pads in the first set to a number of conductors in the second set is typically less than 1:1. For some applications, the ratio is less than 1:20 or even less than 1:100.

There is still further provided, in accordance with an embodiment of the present invention, apparatus including a housing and a set of two or more wires coupled to the housing, each wire having two ends and an intermediate portion, the wires supported by the housing, bent and crossed with one another at the intermediate portion of each wire, so that the intermediate portions of the wires touch each other and so that all of the ends of the wires substantially form a plane, the ends configured to function as electrodes for ablating stratum corneum of skin of a subject when applied to the skin.

There is yet further provided, in accordance with an embodiment of the present invention, apparatus for ablating stratum corneum, including:

a housing;

a set of two or more wires coupled to the housing, each wire having two ends and an intermediate portion, the wires supported by the housing so as not to touch each other; and a coupling element, electrically coupled to the intermediate portion of each of the wires, so that all of the ends of the wires substantially form a plane, the ends configured to function as electrodes for ablating stratum corneum of skin of a subject when applied to the skin.

There is also provided, in accordance with an embodiment of the present invention, a method for facilitating transport of a substance through an area of skin of a subject, the area defining a set of ablation sites, the method including driving current in a sequence into more than one of the ablation sites, the current being capable of ablating stratum corneum of the skin in the ablation sites, so as to facilitate transdermal transport of the substance, the sequence being configured such that, during successive first, second, and third time periods the current is driven into respective first, second, and third ones of the ablation sites, the first ablation site being non-adjacent to the second ablation site, and the second ablation site being non-adjacent to the third ablation site.

Typically, driving the current in the sequence includes configuring the sequence to generally maximize a minimum distance between ablation sites into which current is driven during successive time periods. Alternatively or additionally, a sum of distances between temporally adjacent ones of the ablation sites into which current is driven is typically greater than such sum would be if the sequence is generated randomly.

For some applications, driving the current includes driving the current during 10 successive time periods, the sequence being configured such that a distance between successive sites of application of the current during each of the periods is greater than 1 mm, or even greater than 3 mm.

For some applications, driving the current includes driving the current during at least 10 successive time periods into respective ones of the ablation sites, the sequence being configured such that, for each of the periods, during temporally adjacent ones of the time periods, the current is driven into non-adjacent ablation sites. In an embodiment, driving the current includes configuring the current such that during the at least 10 successive time periods, none of the ablation sites into which current is driven is adjacent to another one of the ablation sites into which current is driven.

There is yet additionally provided, in accordance with an embodiment of the present invention, apparatus for facilitating transport of a substance through an area of skin of a subject, the area defining a set of ablation sites, the apparatus including:

a plurality of electrodes, which are adapted to be placed in contact with the area of the skin at the ablation sites; and a control unit, adapted to drive, during successive first, second, and third time periods, a current capable of ablating stratum corneum of the skin to a first one, a second one, and a third one of the electrodes, the first one of the electrodes being non-adjacent to the second one of the electrodes, and the second one of the electrodes being non-adjacent to the third one of the electrodes, so as to facilitate transdermal transport of the substance.

There is still additionally provided, in accordance with an embodiment of the present invention, a method for facilitating transport of a substance through skin of a subject, including:

applying calibration electrical energy between a first and a second site on the skin, the calibration electrical energy configured such that stratum corneum of the skin is substantially not ablated;

measuring a parameter of the calibration electrical energy;

determining, responsive to the measured parameter, a level of ablating electrical energy capable of ablating stratum corneum of the skin; and applying the ablating electrical energy at the determined level to at least a portion of the skin, so as to facilitate transdermal transport of the substance.

In an embodiment:

applying the calibration electrical energy includes applying the calibration electrical energy between a plurality of first sites and a plurality of respective second sites, measuring the parameter includes measuring the parameter with respect to each of the first sites and the respective second sites, determining the level of ablating electrical energy includes determining the level with respect to each of the first sites and the respective second sites, and applying the ablating electrical energy includes applying the ablating electrical energy at the respective determined levels at each of the respective first and second sites.

For some applications, applying the calibration electrical energy includes applying the energy for less than 200 microseconds.

In an embodiment, applying the voltage drop includes setting the voltage drop to be between about 50 and 100 volts. In this case, measuring the parameter typically includes measuring a level of a current flowing responsive to the voltage drop.

There is also provided, in accordance with an embodiment of the present invention, apparatus for facilitating transport of a substance through skin of a subject, including:

a plurality of electrodes, which are adapted to be placed in contact with the skin; and a control unit, adapted to:

apply calibration electrical energy between a first one and a second one of the electrodes, the calibration electrical energy configured such that stratum corneum of the skin is substantially not ablated, measure a parameter of the calibration electrical energy, determine, responsive to the measured parameter, a level of ablating electrical energy capable of ablating stratum corneum of the skin, and apply the ablating electrical energy at the determined level to at least a portion of the skin, using at least a portion of the electrodes, so as to facilitate transdermal transport of the substance.

There is further provided, in accordance with an embodiment of the present invention, apparatus for application to skin of a subject, including:

a handle;

an electrode cartridge including electrodes which are adapted to be brought in contact with the skin;

a pivot joint coupled to the handle;

a floating element coupled to the handle by the pivot joint and coupled to the electrode cartridge; and a control unit, adapted to detect a displacement of the floating element when force is applied to the electrode cartridge by the skin, and, responsive thereto, to drive through the electrodes current capable of ablating stratum corneum of the skin, so as to facilitate transdermal transport of a substance.

For some applications, the apparatus includes a switch, and the control unit is adapted to detect the displacement of the floating element responsive to a change in state of the switch.

In an embodiment, the handle includes two or more snaps, and the floating element is adapted to be removably coupled to the electrode cartridge by the snaps. In this case, the snaps are typically arranged to: (a) prevent the electrode cartridge from separating from the floating element, and (b) avoid causing a displacement of the floating element sufficient to cause the control unit to drive current through the electrodes.

There is yet further provided, in accordance with an embodiment of the present invention, packaging for storing an electrode-containing element having a plurality of skin-contact electrodes disposed on a skin-contact surface of the element so as to substantially define a skin-contact plane, the packaging including:

a removable cover, disposed so as to substantially define a cover plane; and a container, shaped so as to define an element indentation therein, the element indentation having a bottom surface and shaped to hold the electrode-containing element in a position such that the cover plane and the skin-contact plane of the electrode-containing element form an angle of greater than 5 degrees and less than 90 degrees when the electrode-containing element is stored in the packaging.

In an embodiment, the angle is between about 10 and 35 degrees.

The container typically includes blister packaging.

For some applications, the container is shaped so as to define a handle indentation therein, shaped so as to accept a handle, and so as to guide the handle to accurately couple with the electrode-containing element while the electrode-containing element is in the element indentation.

There is still further provided, in accordance with an embodiment of the present invention, apparatus for application to skin of a subject, including:

a plurality of ablation electrodes, which are adapted to be placed in contact with the skin so as to provide electrical contact with the skin;

at least two driving electrodes, adapted to be passed across the ablation electrodes, so as to create electrical contact between respective ones of the driving electrodes and the ablation electrodes; and a power source, adapted to drive a first one of the driving electrodes to apply current capable of ablating stratum corneum of the skin to a first set of at least one of the ablation electrodes, and to drive a second one of the driving electrodes to apply current capable of ablating stratum corneum of the skin to a second set of at least one of the ablation electrodes, so as to facilitate transdermal transport of a substance.

For some applications, the power source is adapted to:

drive the first one of the driving electrodes to apply the current capable of ablating stratum corneum to the first set of ablation electrodes during a first pass of the driving electrodes across the ablation electrodes, and drive the second one of the driving electrodes to apply the current capable of ablating stratum corneum to the second set of ablation electrodes during a second pass of the driving electrodes across the ablation electrodes.

In an embodiment, the driving electrodes are adapted to be passed across the ablation electrodes so as to create electrical contact with a first one of the ablation electrodes prior to creating electrical contact with a second one of the ablation electrodes.

In an embodiment, the apparatus includes a driving mechanism, adapted to pass the driving electrodes across the ablation electrodes. For example, the apparatus may include a belt, adapted to be coupled to the driving mechanism, the belt including the driving electrodes.

The present invention will be more fully understood from the following detailed description of the preferred embodiments thereof, taken together with the drawings in which:

BRIEF DESCRIPTION OF THE DRAWINGS

FIG. 1 is a schematic, sectional illustration of a handheld device for facilitating transdermal transport of a substance, in accordance with a preferred embodiment of the present invention;

FIG. 4A is a schematic, pictorial illustration of yet another handheld device for facilitating transdermal transport of a substance, in accordance with a preferred embodiment of the present invention;

FIGS. 8A and 8B are schematic illustrations of an electrode set, in accordance with a preferred embodiment of the present invention;

FIGS. 8C and 8D are schematic illustrations of another electrode set, in accordance with a preferred embodiment of the present invention;

FIG. 9 is a schematic sectional side-view illustration of a portion of the electrode set of FIGS. 8A and 8B in electrical contact with a contact board contact, in accordance with a preferred embodiment of the present invention;

FIG. 10 is a schematic sectional illustration of a coupling member electrically coupling the electrode set of FIGS. 8A and 8B or FIGS. 8C and 8D to a contact board contact, in accordance with a preferred embodiment of the present invention;

FIG. 11 is a schematic sectional illustration of an electrode of the electrode set of FIGS. 8A and 8B, in accordance with a preferred embodiment of the present invention;

DETAILED DESCRIPTION OF PREFERRED EMBODIMENTS

Figure 2A:
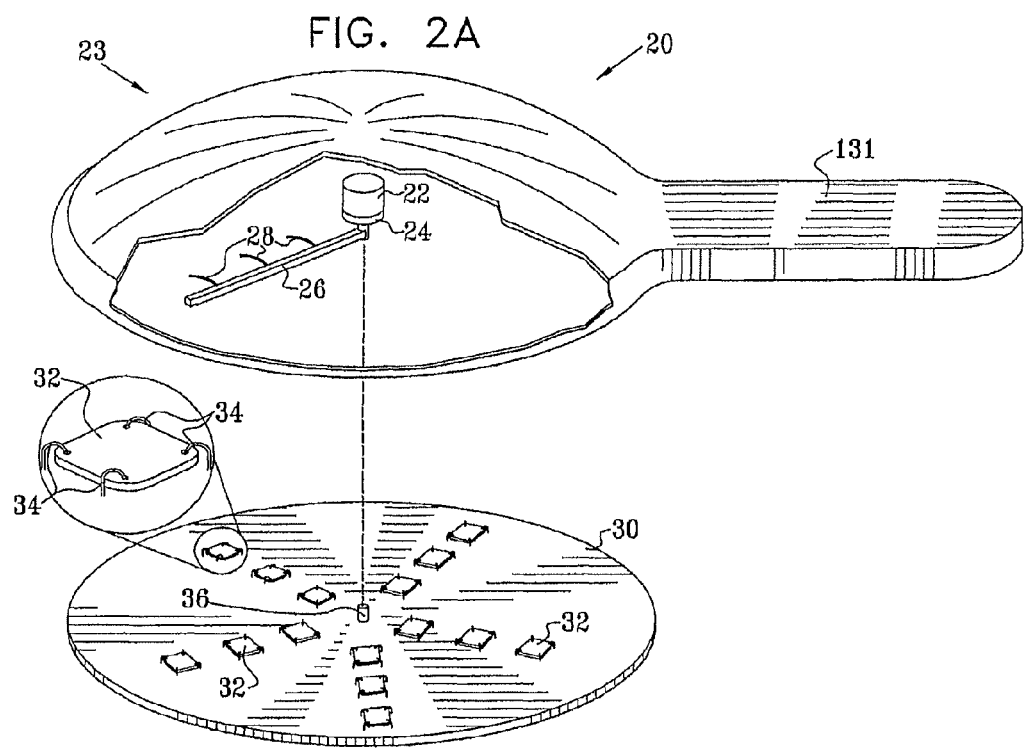
FIG. 2A is a schematic pictorial illustration of a handheld device for facilitating transdermal transport of a substance, in accordance with a preferred embodiment of the present invention.

FIG. 1 is a schematic, sectional illustration of a handheld device 100 for facilitating transdermal transport of a substance, such as a drug, in accordance with a preferred embodiment of the present invention. Device 100 preferably comprises a handle 130, a power unit 102, a control unit 104, and a rotation assembly 114, which is mechanically coupled to a plurality of ablation electrodes 112. Details of some rotation assemblies are described hereinbelow. Although handles, such as handle 130, are shown in FIG. 1A and other figures as elongated elements, this is for the sake of illustration only; embodiments of the present invention include other shapes. In addition, although handles, power units, and control units are shown in the figures as incorporated in an integrated unit, this is for the sake of illustration only. In some embodiments of the present invention, power units and/or control units are located external to handles and are coupled to handles over wires or wirelessly.

Preferably, control unit 104 is electrically coupled to rotation assembly 114 and ablation electrodes 112 by an electrical bus 122, so as to drive a current through ablation electrodes 112. The current is typically configured to cause current flow through skin 150 of a subject or one or more sparks to occur between ablation electrodes 112 and skin 150. Activation of device 100 is initiated when a user activates a power switch 106, such as: (a) a button, which is preferably located at a convenient position on handle 130, or (b) using a switch, as described hereinbelow. Preferably, handle 130 comprises a status indicator 108, such as a status light, which informs the user of the status of device 100, for example when the device is ready to commence electrical treatment and/or when the electrical treatment has been completed. Although applying electrical energy to ablation electrodes is sometimes referred to herein as "applying a voltage," "applying a voltage drop," or "applying a current," it is to be understood that all of these techniques can be used for all applications, except where the context clearly indicates otherwise.

In a preferred embodiment, regulation of the magnitude and timing of the voltage applied to ablation electrodes 112 controls the ablation of stratum corneum 151 of skin 150, so as to improve transdermal delivery of a substance, such as a drug. Preferably, an alternating voltage is applied to ablation electrodes 112, typically having a frequency between about 10 kHz and 4000 kHz, most preferably between about 50 kHz and 500 kHz.

For some applications, the voltage is applied for a fixed length of time, determined in advance to be sufficient to achieve the desired degree of ablation. Alternatively, electrical impedance of the stratum corneum is continuously monitored, and a substantial decrease is interpreted to indicate achievement of a desired level of ablation, whereupon energy application is terminated.

Preferably, each one of ablation electrodes 112 has a contact area with the skin characterized by a diameter of approximately 10-150 microns, typically approximately 60-100 microns. It is noted that this contact area is significantly smaller than that typically used for electroporation applications. For some applications, ablation electrodes 112 function as monopolar electrodes, whereby electrical energy is discharged from ablation electrodes 112 into skin 150, while the return path of the electrical current passes through a much larger surface area (e.g., a metal base surrounding or adjacent to ablation electrodes 112). This typically results in a set of distinct and non-overlapping ablated regions 134 near each ablation electrode 112, but substantially no damage to tissue in other regions between the various ablation electrodes. For example, each ablated area may have a characteristic diameter of about 60-100 microns, and be separated by a distance of about 700-1000 microns from adjacent ablated areas. In a preferred embodiment, for an electrode array which covers a total skin area A, the percentage of skin area A which is ablated is less than about 5%, and is most preferably on the order of about 0.5%.

Alternatively or additionally, when a larger number of ablation electrodes 112 are included in device 100 (e.g., greater than three, or greater than twenty), it is desirable for some applications for one of ablation electrodes 112 to act as an ablation electrode at a particular time, and for two or more of the other electrodes to act, in combination, as non-ablating "return" electrodes, each conveying a fraction of the ablating current back to control unit 104. Further alternatively or additionally, two relatively large return electrodes are provided, functioning as a "split ground."

For some applications, the methods and apparatus of the present invention are carried out in combination with other techniques known in the art for ablating the stratum corneum, such as those described in the above-cited PCT Publication WO 97/07734 to Eppstein et al.

For some applications, electrode cartridge 114 comprises an inkpad 124, which marks the treated region of skin 150 such that a substance-containing patch can be accurately and directly placed on the electrically-treated region after the cartridge has been removed from the region. Alternatively, electrode cartridge 114 has an uneven lower surface, so as to leave temporary dimples on the skin surrounding the treated region of skin 150, thereby facilitating the accurate placement of a substance-containing patch.

Figure 2B:
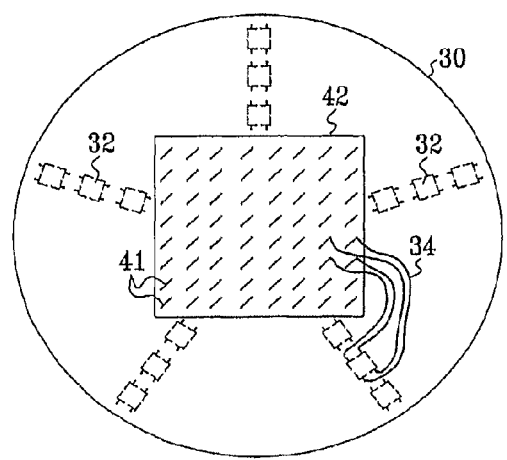
FIG. 2B is a schematic bottom-view of a portion of the device of FIG. 2A, in accordance with a preferred embodiment of the present invention.

Reference is now made to FIGS. 2A and 2B. FIG. 2A is a schematic, pictorial illustration of a handheld device 20 for transdermal transport of a substance, such as a drug, in accordance with a preferred embodiment of the present invention. FIG. 2B is a schematic bottom-view of an electrode board 30 of handheld device 20, in accordance with a preferred embodiment of the present invention. Except for differences described hereinbelow, device 20 is preferably configured to operate generally in accordance with techniques described herein for ablating stratum corneum.

Device 20 comprises a rotation assembly 23, which comprises a rotational energy applicator, such as a motor 22 or a manual crank, to which is coupled a support element, such as a manifold 26, comprising a plurality of driving electrodes 28. Preferably, driving electrodes 28 comprise brush electrodes. A position sensor 24, e.g., positioned adjacent to motor 22 and manifold 26, typically monitors the motion of manifold 26, so as to facilitate the controlled ablation of stratum corneum by ablation electrodes 41 (FIG. 2B) in contact therewith. A handle 131 of device 20 is coupled, preferably removably, to electrode board 30, such as by placing the handle over electrode board 30 and applying pressure on the board from the handle. For some applications, the handle is coupled to the board using clips, such as snaps 412, described hereinbelow with reference to FIG. 15.

Preferably, electrode board 30 comprises an alignment pin 36 to assist in maintaining proper alignment of motor 22 and manifold 26 with electrode board 30. Electrode board 30 preferably further comprises a plurality of contact pads 32, each of which is coupled, through electrode board 30, via leads 34, to one or more ablation electrodes 41 on the lower surface of electrode board 30 (FIG. 2B). For simplicity, FIG. 2B shows the coupling of only one of contact pads 32 to a set of four ablation electrodes 41, however it is to be understood that typically each of the contact pads are coupled to respective sets of one or more ablation electrodes 41. Although leads 34 are shown as wires external to electrode board 30 in FIG. 2B, this is for clarity of illustration only; preferably the leads are incorporated into electrode board 30. Additionally, although only one manifold 26 and corresponding driving electrodes 28 are shown in FIG. 2A, for some applications, a plurality of such manifolds are incorporated into device 20. Ablation electrodes 41 are preferably arranged in a geometry, such as a square 42, that produces an ablated area of the skin suitable for convenient application or extraction of the substance, such as by using a patch. Typically, square 42 has an area of between about 1 and 20 square centimeters.

When a driving electrode contacts a contact pad, and control unit 104 drives power unit 102 (FIG. 1) to power driving electrodes 28 during such contact, the ablation electrodes electrically coupled to that contact pad drive current into skin 150, thereby creating micro-channels in the stratum corneum of the skin. For some applications, all of ablation electrodes 41 are activated in a single rotation of manifold 26.

In a preferred embodiment, electrode board 30 comprises on the order of 1000 ablation electrodes 41, coupled in respective sets of four electrodes to 250 contact pads 32. A smaller number of electrodes 41 and pads 32 are shown in FIGS. 2A and 2B for clarity. By arranging the pads radially outward from the center of electrode board 30 and only having one manifold comprising driving electrodes, only a small fraction of ablation electrodes 41 are activated at any one time, thereby reducing the short-term current requirements on power unit 102. In addition, less than all of driving electrodes 28 may be activated at any given time, further reducing the number of ablation electrodes 41 that are activated at any one time. For example, when the 250 contact pads are divided into 50 radial lines of 5 contact pads each, only 20 ablation electrodes at any instant are typically activated out of the total of 1000. Alternatively, providing driving electrodes 28 with an angular offset, such that the driving electrodes do not fall along a radial line from alignment pin 36, allows for only one contact pad to be activated at a time. This reduces absolute power requirements as well as sensation by the patient. Alternatively or additionally, driving electrodes 28 are not all activated simultaneously. Any one or more of these techniques typically allows for rapid ablation of the skin, while maintaining sufficient spacing between simultaneously-activated ablation electrodes, so as to reduce sensation by the patient.

Figure 3A:
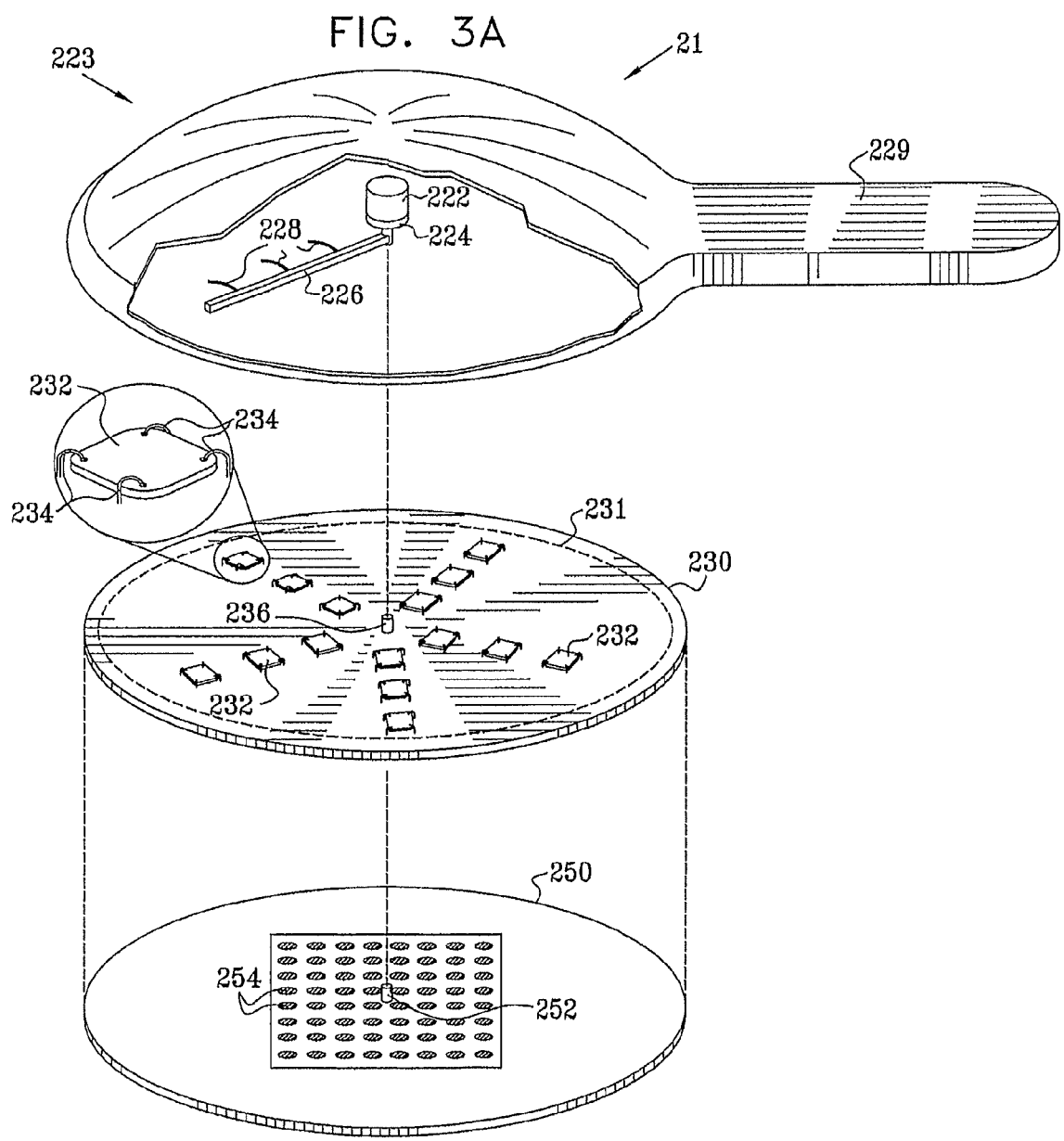
FIG. 3A is a schematic, pictorial illustration of another handheld device for facilitating transdermal transport of a substance, in accordance with a preferred embodiment of the present invention.
Figure 3B:
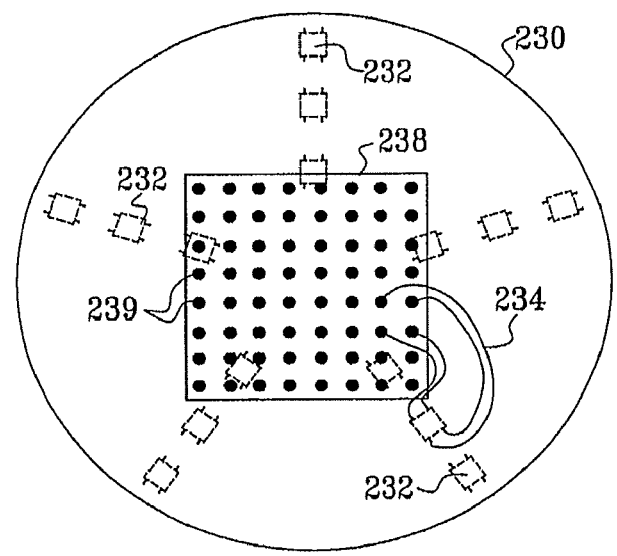
FIG. 3B is a schematic bottom-view of a portion of the device of FIG. 3A, in accordance with a preferred embodiment of the present invention.
Figure 3C:
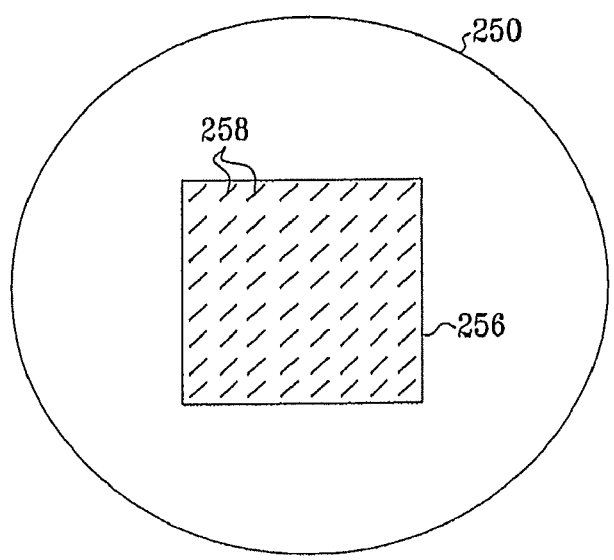
FIG. 3C is a schematic bottom-view of another portion of the device of FIG. 3A, in accordance with a preferred embodiment of the present invention.
Figure 3D:
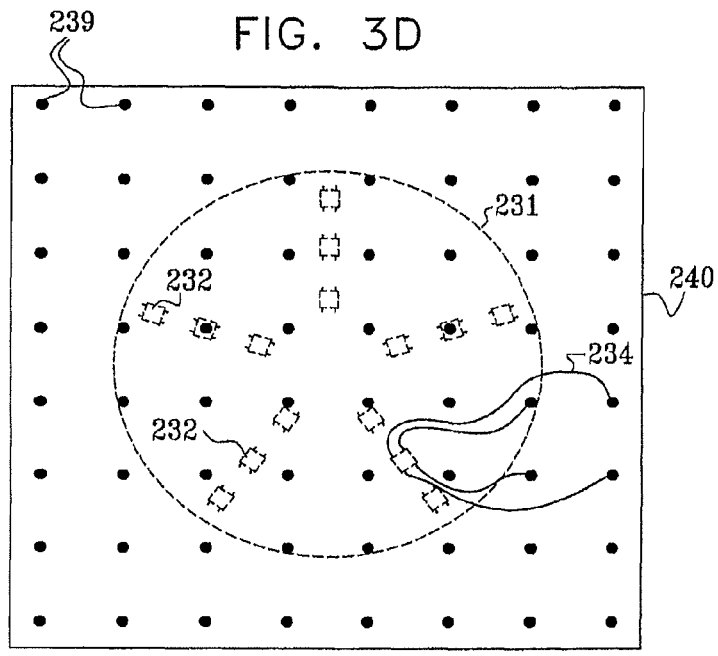
FIG. 3D is a schematic bottom-view of an alternative embodiment of the portion of the device shown in FIG. 3B, in accordance with a preferred embodiment of the present invention.

Reference is now made to FIGS. 3A, 3B, 3C and 3D. FIG. 3A is a schematic, pictorial illustration of a handheld device 21 for facilitating transdermal transport of a substance, such as a drug, in accordance with a preferred embodiment of the present invention. FIG. 3B is a schematic bottom-view of a contact board 230 of handheld device 21, in accordance with a preferred embodiment of the present invention. FIG. 3C is a schematic bottom-view of an electrode cartridge 250 of handheld device 21, in accordance with a preferred embodiment of the present invention. FIG. 3D is a schematic bottom-view of an alternative embodiment of contact board 230 of handheld device 21, in accordance with a preferred embodiment of the present invention. Except for differences described hereinbelow, device 21 is preferably configured to operate generally in accordance with techniques described herein for ablating stratum corneum.

Device 21 comprises a rotation assembly 223, which comprises a rotational energy applicator, such as a motor 222 or a manual crank, to which is coupled a support element, such as a manifold 226, comprising a plurality of driving electrodes 228. Preferably, driving electrodes 228 comprise brush electrodes. Preferably, a position sensor 224, e.g., adjacent to motor 222 and manifold 226, monitors the motion of manifold 226, so as to facilitate the controlled ablation of stratum corneum by ablation electrodes 258 (FIG. 3C) in contact therewith. A handle 229 or other portion of device 21 is coupled to contact board 230. Preferably, contact board 230 comprises an alignment pin 236 to assist in attaining and maintaining proper alignment of motor 222 and manifold 226 with contact board 230. Contact board 230 preferably comprises a plurality of contact pads 232, each of which is coupled via leads 234 to at least one contact board contact 239 on the lower surface of contact board 230 (FIG. 3B). For simplicity, FIG. 3B shows the coupling of only one of contact pads 232 to a set of four contact board contacts 239. Although leads 234 are shown as wires external to contact board 230 in FIG. 3B, this is for clarity of illustration only; preferably, the leads are incorporated into contact board 230.

Handheld device 21 further comprises electrode cartridge 250, which is typically discarded after a single use. Electrode cartridge 250 is removably coupled to handheld device 21, preferably by clipping the electrode cartridge to a lower surface of handle 229 or to a lower surface of contact board 230, using clips, such as snaps 412, described hereinbelow with reference to FIG. 15. Preferably, electrode cartridge 250 comprises an alignment pin 252 to assist in attaining and maintaining proper alignment of the electrode cartridge with contact board 230, motor 222, and manifold 226. The lower surface of electrode cartridge 250 comprises a plurality of ablation electrodes 258 (FIG. 3C), which are placed against skin of the subject. The upper surface of electrode cartridge 250 comprises a plurality of cartridge contacts 254, each of which is electrically coupled, through electrode cartridge 250, to at least one of ablation electrodes 258, preferably to a plurality (e.g., four) of the ablation electrodes.

Ablation electrodes 258 are preferably arranged in a geometry, such as a square 256 (FIG. 3C), that produces an ablated area of the skin suitable for convenient application or extraction of the substance, such as by using a patch. The area of square 256 is typically between about 1 and 20 square centimeters. Cartridge contacts 254 (FIG. 3A) are preferably arranged in substantially the same arrangement as the ablation electrodes, on the other side of ablation cartridge 250, so that each cartridge contact 254 corresponds to and is located in a vicinity of one or more ablation electrodes 258 (FIG. 3C). For the sake of illustration only, a one-to-one correspondence between cartridge contacts 254 and ablation electrodes 258 is shown in FIGS. 3A and 3C. The arrangement of cartridge contacts 254 (FIG. 3A) and contact board contacts 239 (FIG. 3B) are substantially the same, so as to enable electrical contact between corresponding contacts when the lower surface of contact board 230 and the upper surface of electrode cartridge 250 are brought into contact with one another.

Although contact board contacts 239 are shown as arranged in a square 238, the area of which is smaller than an area 231 (FIG. 3A) that encompasses contact pads 232, this is for the sake of illustration only. For some applications, contact board contacts 239 are arranged in an arrangement, such as a square 240 (FIG. 3D), the area of which is larger than area 231.

Figure 3E:
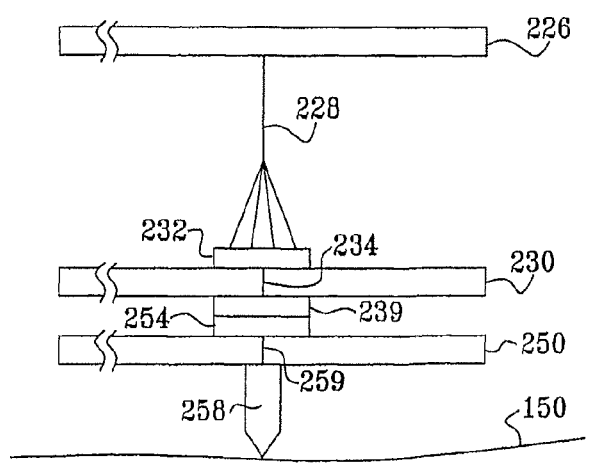
FIG. 3E is a schematic, sectional side-view illustration of an example electrical path through the device of FIG. 3A, in accordance with a preferred embodiment of the present invention.

Reference is now made to FIG. 3E, which is a schematic, sectional side-view illustration of an example electrical path through handheld device 21, in accordance with a preferred embodiment of the present invention. Current travels over the following path from manifold 226 to skin 150:

(a) current is applied to driving electrode 228, a brush portion of which makes physical and electrical contact with contact pad 232;
(b) contact pad 232 is electrically coupled to at least one contact board contact 239, by at least one lead 234, which passes through contact board 230;
(c) contact board contact 239 makes physical and electrical contact with cartridge contact 254, which is electrically coupled to at least one ablation electrode 258, by at least one lead 259, which passes through electrode cartridge 250; and
(d) ablation electrode 258 applies the current to skin 150.

In a preferred embodiment, electrode cartridge 250 comprises on the order of 1000 ablation electrodes 258, coupled in respective sets of four ablation electrodes to 250 electrode contacts 254. A smaller number of ablation electrodes 258 and contact pads 232 are shown in FIGS. 3A, 3B, 3C, and 3D for clarity.

Figure 4B:
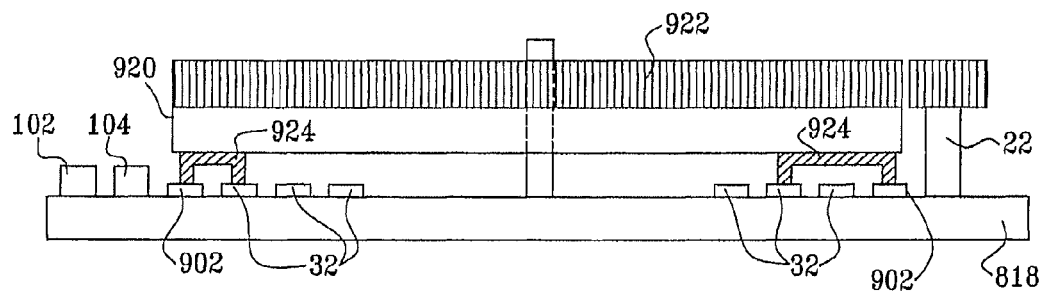
FIG. 4B is a schematic side-view illustration of a portion of an alternative embodiment of the handheld device shown in FIG. 4A, in accordance with a preferred embodiment of the present invention.
Figure 4C:
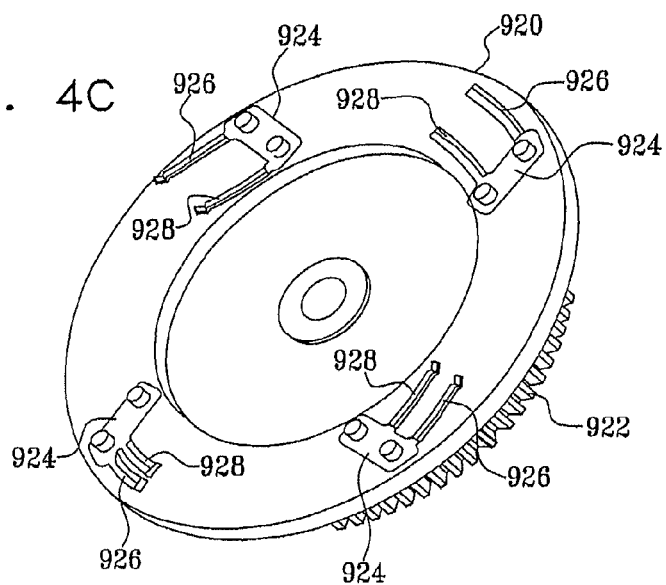
FIG. 4C is a schematic illustration of a power transfer disk, in accordance with a preferred embodiment of the present invention.

FIGS. 4A, 4B, and 4C are schematic illustrations of a handheld device 900 for enabling transdermal transport of a substance, such as a drug, in accordance with a preferred embodiment of the present invention. Handheld device 900 is generally similar to handheld device 20, as described hereinabove with reference to FIGS. 2A and 2B, and, except for differences described hereinbelow, handheld device 900 is preferably configured to operate generally in accordance with techniques described herein for ablating stratum corneum, including with apparatus and techniques described hereinabove with reference to FIGS. 3A, 3B, 3C, 3D and 3E. In particular, although handheld device 900 is described hereinbelow as comprising an electrode board 818, for some applications handheld device 900 instead comprises a contact board and an electrode cartridge, as described hereinabove with reference to FIGS. 3A, 3B, 3C, 3D and 3E.

FIG. 4A shows a particular preferred configuration for bringing power to contact pads 32. In this configuration, electrode board 818 (configuration shown) or the handle (configuration not shown) comprises a plurality of power tracks 902, e.g., three or four, preferably corresponding to the number of driving electrodes 912 and/or the number of contact pads 32 in each line extending radially from pin 36. The power tracks are coupled by power transfer elements 910 to contact pads 32. A first end of each power transfer element 910 comprises one of track contacts 908, which comes in electrical contact with power tracks 902 as the power transfer element rotates. A second end of each power transfer element 910 comprises one of driving electrodes 912, which comes in electrical contact with at least a portion of contact pads 32 as the power transfer element rotates. Track contacts 908 and driving electrodes 912 preferably comprise brush electrodes. Although only one power transfer element 910 is shown for clarity, three such elements 910 are preferably coupled to each of one or more rotational members 906 in the illustrated configuration. Preferably, control unit 104 supplies power from power unit 102 to less than all of power tracks 902 at a time, over power leads 914, such that typically only one radial line of contact pads 32 is activated at any given time. For some applications, power is supplied to only one power track 902 at a time. For applications in which handheld device 900 comprises the same number of driving electrodes 912 as power tracks 902, control unit 104 typically selectively actives contact pads 32 by powering the appropriate power track at the appropriate time.

For some applications, power unit 102 and/or control unit 104 are fixed to electrode board 818 (configuration not shown), and not to handle 130. For some applications, power tracks 902 are fixed above rotational members 906 (and not to electrode board 818), but otherwise operate in substantially the same manner as described hereinabove (configuration not shown).

FIG. 4B is a schematic side-view illustration of a portion of an alternative embodiment of handheld device 900, in accordance with a preferred embodiment of the present invention. FIG. 4C is a schematic illustration of a power transfer disk 920, in accordance with a preferred embodiment of the present invention. One or more of control unit 104, power unit 102, and motor 22 are fixed to electrode board 818, instead of to handle 130. Instead of rotational members 906, handheld device 900 comprises power transfer disk 920, which typically comprises gear teeth 922 arranged around the circumference of the power transfer disk. Motor 22, whether fixed to electrode board 818 or handle 130, engages gear teeth 922 and drives rotation of the power transfer disk.

On its lower surface, power transfer disk 920 comprises a plurality of power transfer elements 924. Each power transfer element 924 typically comprises a track contact 926 at a first end of the element, and at least one driving electrode 928 at a second end of the element. Track contact 926 and driving electrode 928 of each power transfer element are directly electrically connected to each other, typically but not necessarily because each power transfer element 924 is formed from a single piece of metal. Track contact 926 is aligned so as to come in electrical contact with power tracks 902 as the power transfer disk rotates. Each of driving electrodes 928 is typically aligned to come in contact with at least one contact pad 32 as the power transfer disk rotates. For example, each of the driving electrodes may sequentially come in contact with a respective plurality of contact pads 32, each disposed at a certain distance from the center of the power transfer disk. Thus, FIG. 4C shows track contact 926 of each power transfer element 924 at a fixed radius from the center of the power transfer disk, while driving electrodes 928 of each power transfer element 924 are at different respective distances from the center of the power transfer disk.

Control unit 104 drives motor 22 to rotate power transfer disk 920, and typically selectively applies power to power tracks 902 based on the rotational position of the disk, so as to selectively power contact pads 32.

Figure 5:
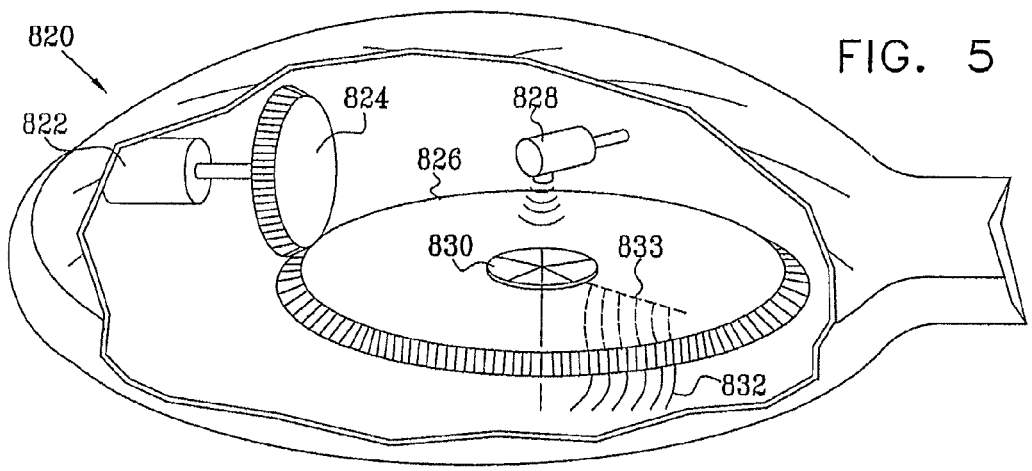
FIG. 5 is a schematic illustration of a rotation assembly, in accordance with a preferred embodiment of the present invention.

FIG. 5 is a schematic illustration of a rotation assembly 820, in accordance with a preferred embodiment of the present invention. Rotation assembly 820 is adapted to be used instead of the rotation assemblies described hereinabove with reference to FIGS. 2A, 3A and 4A. Rotation assembly 820 comprises a rotating disk 826 that is rotationally driven by a driving gear 824, preferably using friction or teeth that mesh with corresponding teeth on the edge of disk 826. Driving gear 824 is powered by a rotational energy applicator, such as a motor 822 or a manual crank. A position sensor 828, preferably positioned over the vicinity of the center of disk 826, monitors the motion of disk 828, so as to facilitate controlled ablation of stratum corneum by the handheld device. In a preferred embodiment, position sensor 828 comprises an optical sensor, which detects motion of an optical disk 830, preferably positioned in the center of disk 826. For example, optical disk 830 may be marked with a pattern of radial lines that are detected by the optical sensor. Alternatively, position sensor 828 comprises a dedicated brush that passes over dedicated position-indicating pads (not shown) on electrode board 818.

A plurality of driving electrodes 832 are arranged in one or more radial lines 833 (only one such line is shown in FIG. 5 for clarity of illustration), and electrically coupled to a control unit (not shown). Using input from position sensor 828, the control unit typically precisely controls the timing of activating driving electrodes 832 in order to increase the likelihood that each driving electrode is in good electrical contact with its target contact pad at the instant of activation and for the duration of current application. The control unit typically attempts to activate a driving electrode when the driving electrode is in contact with the middle of a contact pad. If this precise location is not achieved, e.g., because of manufacturing or operation variances, the driving electrode still typically makes good electrical contact with a region of the contact pad other than its middle.

Figure 6A:
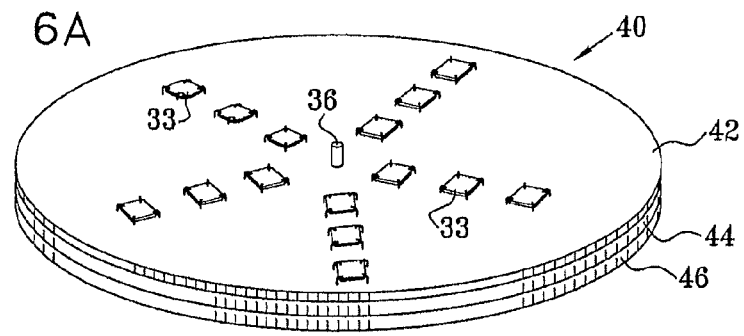
FIG. 6A is a schematic illustration of a printed circuit board (PCB) for use with the devices shown in FIGS. 1, 2A, 3A, and 4A, in accordance with a preferred embodiment of the present invention.
Figure 6B:
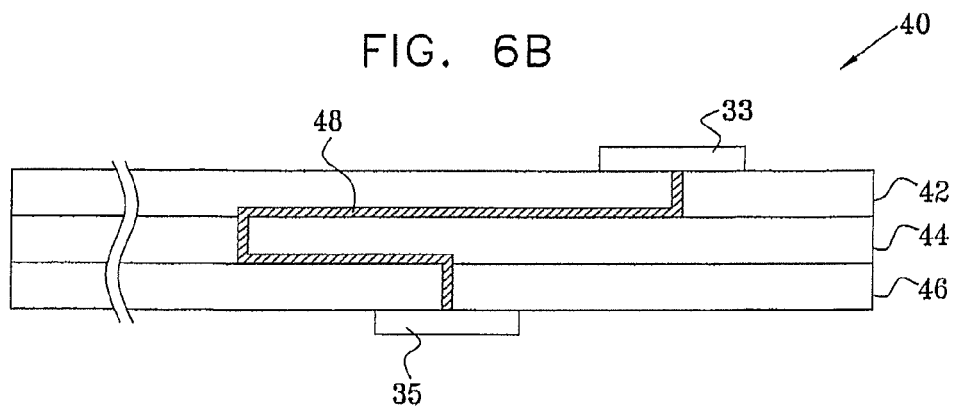
FIG. 6B is a schematic, sectional side-view of a portion of the PCB of FIG. 6A, in accordance with a preferred embodiment of the present invention.

Reference is now made to FIGS. 6A and 6B. FIG. 6A is a schematic illustration of a printed circuit board (PCB) 40 for use with the handheld devices shown in FIGS. 1, 2A, 3A, and 4A, in accordance with a preferred embodiment of the present invention. FIG. 6B is a schematic, sectional side-view of a portion of PCB 40, in accordance with a preferred embodiment of the present invention. PCB 40 is generally similar to electrode board 30, described hereinabove with reference to FIGS. 2A and 4A, and contact board 230, described hereinabove with reference to FIG. 3A. Thus, the lower surface of PCB 40 comprises either contacts or electrodes, as appropriate. Except for differences described hereinbelow, PCB 40 is preferably configured to operate generally in accordance with some or all of the techniques described herein for ablating stratum corneum.

PCB 40 comprises a plurality of layers 42, 44 and 46. Although only three layers are shown in FIG. 6 for clarity of illustration, PCB 40 typically comprises a greater number of layers, e.g., about four to eight layers. The upper surface of PCB comprises a plurality of contact pads 33, which are similar to contact pads 32, described hereinabove with reference to FIGS. 2A and 4A, and contact pads 232, described hereinabove with reference to FIG. 3A.

As is best seen in FIG. 6B, each contact pad 33 is electrically coupled to at least one conductor 35, over one or more traces 48, as is known in the art of PCB design and fabrication. Conductor 35 comprises either a contact, as described hereinabove with reference to FIGS. 2A and 4A, or an ablation electrode, as described hereinabove with reference to FIG. 3A. The use of a PCB, particularly a multi-layered PCB, allows conductors 35 to be readily placed at locations other than in the vicinity of the respective contact pads to which they are electrically coupled, using PCB design techniques known in the art.

Figure 7A:
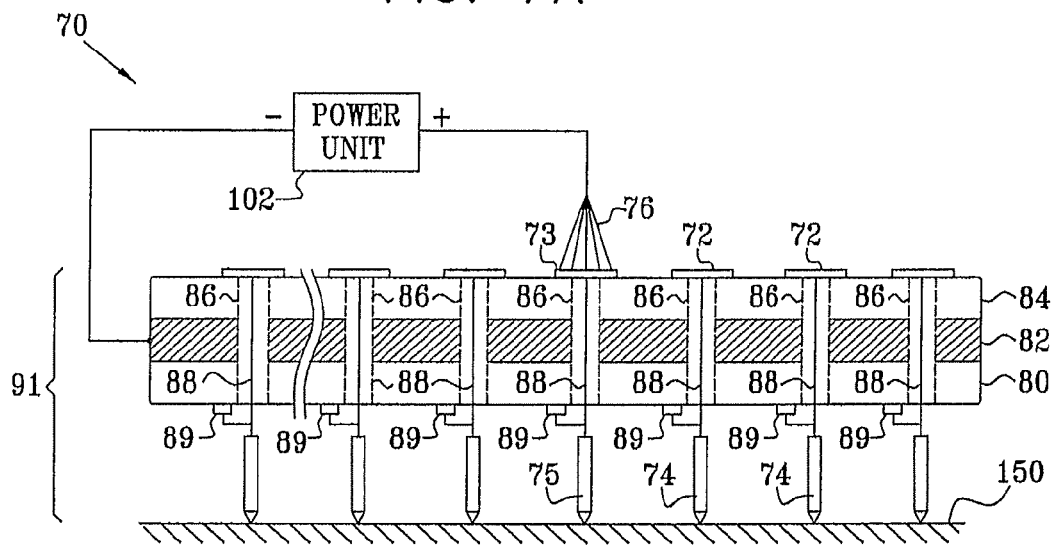
FIG. 7A is a schematic sectional illustration of a PCB assembly for use with the devices shown in FIGS. 1, 2A, 3A and 4A, in accordance with a preferred embodiment of the present invention.
Figure 7B:
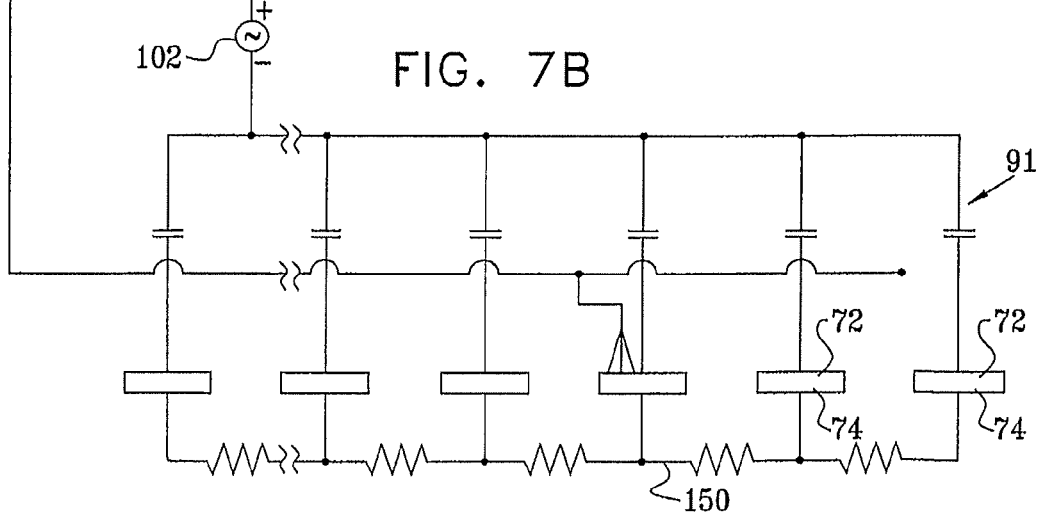
FIG. 7B is a schematic illustration of a circuit representing the PCB assembly of FIG. 7A, in accordance with a preferred embodiment of the present invention.

Reference is now made to FIGS. 7A and 7B. FIG. 7A is a schematic sectional illustration of a PCB assembly 70, for optional use with the handheld devices described hereinabove with reference to FIGS. 1, 2A, 3A, and 4A, in accordance with a preferred embodiment of the present invention. FIG. 7B is a schematic illustration of a circuit representing PCB assembly 70, in accordance with a preferred embodiment of the present invention. PCB assembly 70 is generally used in a similar manner to PCB 40, as described hereinabove with reference to FIGS. 6A and 6B. PCB assembly 70 comprises at least two non-conducting layers, an upper non-conducting layer 84 and a lower non-conducting layer 80. Upper non-conducting layer 84 and lower non-conducting layer 80 are separated by a conducting layer 82. Upper non-conducting layer 84 has coupled thereto a plurality of contact pads 72, which are exposed on the top surface of the upper non-conducting layer. The contact pads are electrically coupled to ablation electrodes 74 by leads 88, which travel through channels 86, such as vias, shown in FIG. 7A as vertical holes demarcated by dashed lines. Channels 86 thus electrically isolate leads 88 from conductive layer 82. Additionally, each lead 88 is electrically coupled to the bottom surface of lower layer 80 in the vicinity of the respective electrode 75.

It is to be understood that PCB assembly 70 has been described herein and shown in FIG. 7A with only two non-conducting layers for simplicity of illustration only; generally PCB 70 comprises more than two non-conducting layers, as described hereinabove with reference to FIGS. 6A and 6B. In addition, although channels 86 are shown as simple vertical channels, they may follow a more complex route through the layers of the PCB. In addition, although PCB assembly 70 is described and shown as comprising ablation electrodes 74, this is for the sake of illustration only; PCB assembly 70 can also comprise contact board contacts, as described hereinabove with reference to FIG. 3A.

Conducting layer 82 serves as a ground, and as such is electrically coupled to a ground terminal of power unit 102. Lower non-conducting layer 80 and/or upper non-conducting layer 84 naturally form the dielectric of a capacitive element 91, in which conducting layer 82 is separated from electrodes 74 (and/or skin 150, contact pads 72, or conductors in electrical contact with electrodes 74). Therefore, handheld devices that comprise PCB assembly 70 in this configuration do not necessarily comprise a return electrode that is specifically designated to function as a ground. Instead, all of electrodes 75 are preferably given a small capacitance to ground, by virtue of one or more of the following:

(a) electrical coupling of the electrodes to lower-layer contacts 89, in the vicinity of each respective electrode, and the resultant capacitive coupling between lower-layer contacts 89 and conductive layer 82, (b) capacitive coupling between skin 150, in the region of electrodes 74, and conductive layer 82, and (c) capacitive coupling between contact pads 72 (which are electrically coupled to electrodes 74) and conductive layer 82.

For some applications, PCB assembly 70 comprises a plurality of conducting layers 82, separated from each other by respective non-conducting layers (configuration not shown). Each non-conducting layer comprises a plurality of contacts 89 typically integrated within the non-conducting layer, with each of the contacts directly electrically coupled to a respective pad 72. Typically, each pad 72 is directly electrically coupled to a plurality of contacts 89 located within respective non-conducting layers. Such a configuration generally linearly multiplies the total amount of capacitance. In one particular configuration, PCB assembly 70 comprises four conducting layers 82, and each pad 72 is coupled to four contacts 89, located within respective non-conducting layers. For these applications, contacts 89 generally have a characteristic of about 0.5-4 mm2, and are separated from the nearest conducting layer 82 by about 0.1-0.3 mm.

Since only a small fraction of the ablation electrodes are energized at any one time, the remaining electrodes function as return paths through capacitive element 91 to ground. Preferred values for the capacitance provided by each of the electrodes preferably corresponds to an impedance of, for example, 500 kilo-ohm to 2 mega-ohm for each electrode at the operating frequencies. In this manner, the overall impedance is typically in the range of about 0.5 kilo-ohm to 2 kilo-ohm if 1000 ablation electrodes 74 are used.

Typically, the capacitance to ground provided by any one of the electrodes is not so high as to constitute a short circuit in the frequencies of the current application, when that electrode is in contact with a driving electrode, because the impedance to ground through that electrode is typically greater than 500 kilo-ohm.

Alternatively, capacitive element 91 comprises discrete capacitors and/or resistors, coupled to each of the ablation electrodes and to conducting layer 82 (configuration not shown).

When a brush electrode 76 is brought into electrical contact with a contact pad 73, current is driven to electrode 75. Most of this current is delivered to skin 150, but a relatively small portion of the current leaks capacitively to ground through capacitive element 91 in the vicinity of electrode 75. A substantial portion of the current (typically, at least 80%) travels through skin 150 and returns to ground through the other electrodes 74.

Reference is now made to FIGS. 8A and 8B, which are schematic illustrations of an electrode set 160, in accordance with a preferred embodiment of the present invention. FIG. 8A shows a perspective side-view of electrode set 160, and FIG. 8B shows a bottom-view of the electrode set. Electrode set 160 is preferably used with handheld device 21 (described with reference to FIG. 3A), or with the handheld devices described hereinabove with reference to FIGS. 1, 2A, and 4A. Each electrode set preferably comprises at least two wires, for example two wires, wire 180 and a wire 182, which are bent (e.g., in the shape of a parabola, as shown, or in the shape of a conventional staple, not shown) and crossed with one another at an intersection point 172 (which is about at the middle of each wire), such that the four ends of the two wires substantially form a plane, and define ablation electrodes 178. For some applications, electrode set 160 comprises three or more wires (not shown). The wires are preferably formed by extrusion. Preferably, cone- or pyramid-style pieces 174 (or pieces having other shapes) surround and support electrodes wires 180 and 182, such that the electrode portions of the wires protrude from the cones or pyramids. Typically, wires 180 and 182 are not mechanically secured to one another, but rather are held in electrical contact with each other by virtue of the natural mechanical properties of the wires when supported by pieces 174. Alternatively, the wires are mechanically coupled to one another at intersection point 172. Preferably, the diameter of the wires is between about 40 and 200 microns.

FIGS. 8C and 8D are schematic illustrations of an alternate embodiment of electrode set 160, in accordance with a preferred embodiment of the present invention. In this embodiment, wires 180 and 182 are bent (e.g., in the shape of a conventional staple, as shown, or in the shape of a parabola, not shown), but are not crossed, unlike the embodiment described hereinabove with reference to FIGS. 8A and 8B. Instead, a connecting portion 190 of a coupling member 183 is placed on each of the wires, at points 179 and 181, electrically coupling the wires together. (Coupling member 183 is described hereinbelow with reference to FIG. 10.) As in the embodiment shown in FIG. 8A, the four ends of the two wires substantially form a plane, and define ablation electrodes 178. Coupling member 183 passes through a hole 192 defined by electrode cartridge 250.

FIG. 9 is a schematic sectional side-view illustration of a portion of electrode set 160 in electrical contact with a contact board contact 239, in accordance with a preferred embodiment of the present invention. This embodiment is typically employed with the embodiment of electrode set 160 illustrated in FIGS. 8A and 8B. Pieces 174 are attached to or incorporated into the lower surface of electrode cartridge 250 (FIG. 3C). When the upper surface of electrode cartridge 250 (FIG. 3A) is brought in contact with the lower surface of contact board 230 (FIG. 3B), as described hereinabove with reference to FIGS. 3A, 3B and 3C, wire 180 makes electrical contact with contact board contact 239 in the vicinity of point 172. The pressure applied between electrode cartridge 250 and contact board 230 cause wire 180 to flex slightly, generally resulting in good electrical contact between wire 180 and contact board contact 239. Preferably, the pressure required to make good electrical contact between each electrode set and the corresponding contact board contact is relatively low, typically between about 0.5 and 4 grams. As a result, a typical user of the handheld device is reasonably able to apply the total pressure (equal to the sum of the pressure applied to each individual electrode set) necessary to couple the electrode cartridge to the contact board. For example, in embodiments of the device comprising 200 electrode sets, the total pressure that would be applied could be 200 grams.

Preferably, the portion of wire 180 that protrudes from the upper surface of electrode cartridge 250 has an unflexed height $L_1$ (i.e., a height prior to compression by contact board contact 239) of between about 0.1 and 1 millimeter, and a flexed height $L_1$ of between 0 and 0.5 millimeters. The pieces preferably have a height $L_2$ of between about 0.1 and 1 millimeters. Preferably, the portion of wires 180 and 182 that protrudes from cone-style pieces 174, and comprises electrodes 178, has a length $L_3$ of between about 0.02 and 0.20 millimeters. Electrodes 178 of wire 180 are preferably spaced a distance $L_4$ of between about 0.7 and 1.0 millimeters from each other. Preferably, electrode sets 160 are spaced with a density of between about 50 and 200 electrodes per square centimeter.

FIG. 10 is a schematic sectional illustration of coupling member 183 electrically coupling the electrode set of FIGS. 8A and 8B or FIGS. 8C and 8D to a contact board contact 239, in accordance with a preferred embodiment of the present invention. In the case of the electrode set of FIGS. 8A and 8B, one end of coupling member 183 is in contact with wire 180 at intersection point 172. (Wire 180 in turn is in contact with wire 182, also at intersection point 172.) In the case of the electrode set of FIGS. 8C and 8D, this end of coupling member 183 is in contact with both wires 180 and 182 at connecting portion 190, as best seen in FIG. 8C. The other end of coupling member 183, which is preferably hooked or otherwise shaped to increase its contact surface area, makes electrical contact with contact board contact 239 when the upper surface of electrode cartridge 250 (FIG. 3A) is brought in contact with the lower surface of contact board 230 (FIG. 3B), as described hereinabove with reference to FIGS. 3A, 3B and 3C. The length $L_5$ of coupling member 183 is preferably between about 5.0 and 12.0 millimeters. The diameter of coupling member 183 is preferably between about 20 and 60 microns.

FIG. 11 is a schematic sectional illustration of one of electrodes 178, in accordance with a preferred embodiment of the present invention. Wire 180, as it passes through cone- or pyramid-style piece 174 in this embodiment, comprises an angular bend 185, such as a crimp. Angular bend 185 typically serves to maintain a constant length $L_3$ of electrode 178, despite upward and/or downward pressure that may be applied to electrode 178 during use. Use of an angular bend 185 is particularly useful in supplementing the reduced friction force when wire 180 has a diameter less than about 100 microns, and, even more so when the diameter is less than about 60 microns.

Figures 12, 13:
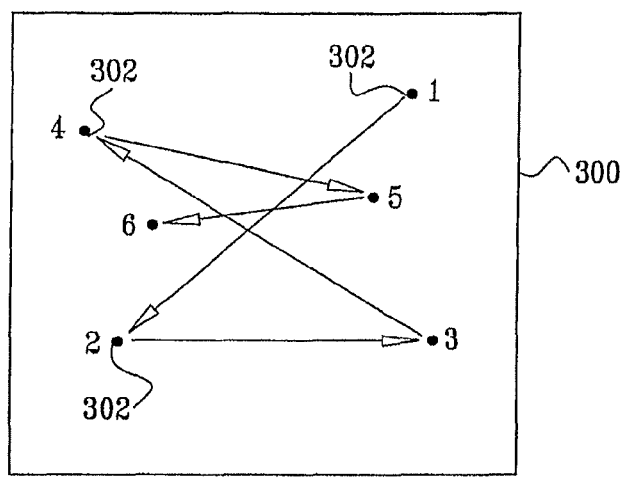
FIG. 12 is a schematic illustration of a method for sequencing the activation of electrodes, in accordance with a preferred embodiment of the present invention.
FIG. 13 is a schematic illustration of a method for generating an activation sequence, in accordance with a preferred embodiment of the present invention.

FIG. 12 is a schematic illustration of a method for sequencing the activation of electrodes 302, in accordance with a preferred embodiment of the present invention. Electrodes 302, distributed over an area 300, are activated in an activation sequence pursuant to which the distances between each activated electrode and the successively-activated electrode are generally greater than such distances would be pursuant to a random activation sequence.

For example, the group of six electrodes 302 shown in FIG. 12 is activated in the sequence indicated by the numbers with which each electrode is labeled. For some applications, the activation sequence is selected from a set of potential activation sequences by calculating, for each potential activation sequence, the sum of the distances between successively-activated electrodes, and selecting the potential activation sequence that has the greatest sum. Larger distances between successively-activated electrodes generally minimizes any sensation of pain or discomfort that a subject might experience during ablation.

The sequence is preferably configured to attempt to maximize both the average distance between activated electrodes and the minimum distance between activated electrodes. Should maximizing the average distance and maximizing the minimum distance come in conflict, then maximizing the minimum distance between activated electrodes typically takes higher priority.

FIG. 13 is a schematic illustration of a method for generating an activation sequence, as described with reference to FIG. 12, in accordance with a preferred embodiment of the present invention. According to this method, area 300 is divided into rectangular regions 310, such as square regions, arranged in a grid. During ablation, the device cycles through the regions 310, so that successively-activated regions are in most instances at least a minimum threshold distance apart, and activates an electrode 302 in each region. The sequence is typically cycled through at least twice, with a different electrode in each region preferably activated each time the sequence is repeated. Since sequential regions are generally at least the minimum threshold distance apart, each electrode within a region is at least the minimum threshold distance apart from the electrode activated in the next region in the sequence. Therefore, the sequence of activating electrodes within a given region during successive cycles of the sequence is generally not important, which affords flexibility in designing a contact board.

In a preferred embodiment, sequential regions are separated by at least one intervening region, or are at least the distance of a "knight's jump" (as in a game of chess) from one another, i.e., at least one column or row in a first direction, and at least two columns or rows in a second direction perpendicular to the first direction. In other words, sequential regions are not adjacent to one another, including not diagonally adjacent. For example, an electrode in region 1 (column D, row 1) is activated first. Next, an electrode in region 2 (column C, row 3), which is one column and two rows removed from region 1, is activated. Similarly, region 3 (column A, row 2) is a knight's jump from region 2. Note that region 8 (column C, row 2) is more than a knight's jump from region 7 (column A, row 4), which relative location satisfies the general minimum distance requirements of this sequencing method. After an electrode has been activated in all sixteen regions of this example, the sequence is repeated beginning with region 1, which is also labeled region 17 to illustrate this repetition. It is to be noted that this activation strategy is exemplary, and other strategies will be readily apparent to those skilled in the art, having read the present patent application. The sequence is preferably configured to attempt to maximize both the average distance between activated electrodes and the minimum distance between activated electrodes.

Preferably, after a desired activation sequence of electrodes is determined (optionally using the method described with reference to FIG. 13), in order to implement the sequence using the handheld devices described herein, one of the following techniques, or, most preferably, both in combination, are used. Techniques for achieving a desired activation sequence using other skin ablation devices will be evident to those skilled in the art, having read the present patent application.

The handheld device comprises power tracks 902, as described hereinabove with reference to FIG. 4A. Power is supplied to only one power track 902 at a time. A power track generally provides power to only one power transfer element at a time, because only one power transfer element is typically in contact with a given power track at any time. Activating different power tracks in sequence drives current into the skin through a number of power transfer elements in sequence, allowing for the rapid selection of ablation sites in different sections of the ablation area, thereby achieving a distributed activation sequence.

The handheld device comprises a multi-layered PCB, such as that described hereinabove with reference to FIGS. 6A and 6B. Design of the PCB allows electrodes to be readily placed at locations other than in the vicinity of their corresponding contact pads. These locations are selected in order to achieve a distributed activation sequence.

Figure 14:
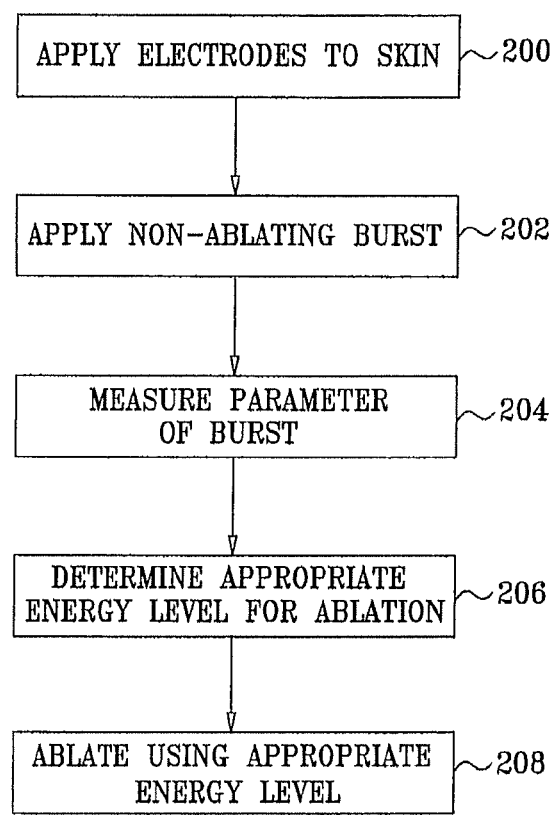
FIG. 14 is a flow chart that schematically illustrates a method for calibrating a voltage, in accordance with a preferred embodiment of the present invention.

FIG. 14 is a flow chart that schematically illustrates a method for calibrating a voltage, in accordance with a preferred embodiment of the present invention. When forming micro-channels in the stratum corneum, it is generally desirable to apply the minimum energy necessary to successfully form the micro-channels. Minimizing the applied energy reduces device energy requirements, which is particularly beneficial for battery-operated devices. Applying less energy may also reduce any sensation a subject might feel during ablation. While an appropriate voltage to apply can be pre-configured for an ablation device, it is desirable in some applications to calibrate the applied voltage at least once per use of the device. Such repeated calibration is beneficial because the impedance of stratum corneum varies from subject to subject, and even from time to time within a given subject (for example, because of varying moisture levels of the stratum corneum). Furthermore, for some applications, it is desirable to separately calibrate the applied voltage for each of one or more ablation electrodes in an array of electrodes, because the impedance of stratum corneum sometimes varies even over a small area of skin.

In a preferred embodiment, this calibration is performed using a technique of "feed-forward," as follows. A set of ablation electrodes is applied to the skin of the subject, at an electrode application step 200. Using at least one ablation electrode, a brief calibration burst of energy in applied to the stratum corneum, at a non-ablating burst application step 202. (One or more appropriate return electrodes or other return contact surfaces are used.) The calibration burst is applied at a relatively low energy level, such that ablation substantially does not occur, or occurs to a small extent compared to subsequently-applied ablation, and no sensation is typically felt by the subject. For some applications, the calibration burst is applied as a low current, a low voltage, or even a relatively-high voltage applied for a short duration (e.g., less than 500 microseconds or even less than 200 microseconds). The calibration burst is preferably applied by applying a voltage drop between the at least one ablation electrode and the return electrodes, typically, but not necessarily, a peak voltage drop of between about 50 and 100 volts. Alternatively, the calibration burst is applied using a known current, in which case a peak current of between about 0.1 and 0.5 mA is typically applied. A parameter of the calibration burst is measured, at a parameter burst measurement step 204, which preferably is performed simultaneously with step 202 (step 204 is shown in FIG. 14 subsequent to step 202 for clarity of illustration only). When the calibration burst is applied by applying a voltage drop, the parameter preferably is an amperage of a current generated as a result of the application of the voltage drop. On the other hand, when the calibration burst is applied by applying a current, the parameter preferably is a measure of a voltage drop. The parameter is generally indicative of a level of impedance in the electrode/skin contact area of the stratum corneum, combined with impedance of the electrodes and associated apparatus. Responsive to the measured parameter, an appropriate energy level, such as a voltage or an amperage, to use for subsequent ablation is determined, at an energy level determination step 206. Using this energy level, ablation is performed, at an ablation step 208.

In a preferred embodiment, steps 202 through 208 are repeated in real-time for each of a plurality of ablation electrodes of the array, each time ablation is applied. Applying the calibration burst and measuring the parameter (steps 202 and 204) are preferably performed in less than about 1 millisecond, and ablation is preferably applied (step 208) for less than about 4 milliseconds, most preferably for less than about 1 millisecond. Typically, any given contact pad is electrically coupled to the control unit for about 1 to 25 milliseconds.

Alternatively, steps 202 through 208 are performed only once, at the commencement of an ablation procedure, using a single ablation electrode or a plurality of electrodes. A single calibrated energy level is determined, and this energy level is preferably used for all of the ablation electrodes activated during the ablation procedure. Because the natural impedance of stratum corneum prior to ablation is relatively high, using a plurality of electrodes typically results in a more accurate measurement of impedance because total current is greater than if only a single ablation electrode were to apply a single sub-ablation calibration voltage. For some applications, this energy level calibration procedure is combined with an impedance-sensing procedure performed in order to determine initial contact of the electrode array with the skin of the subject.

Figure 15:
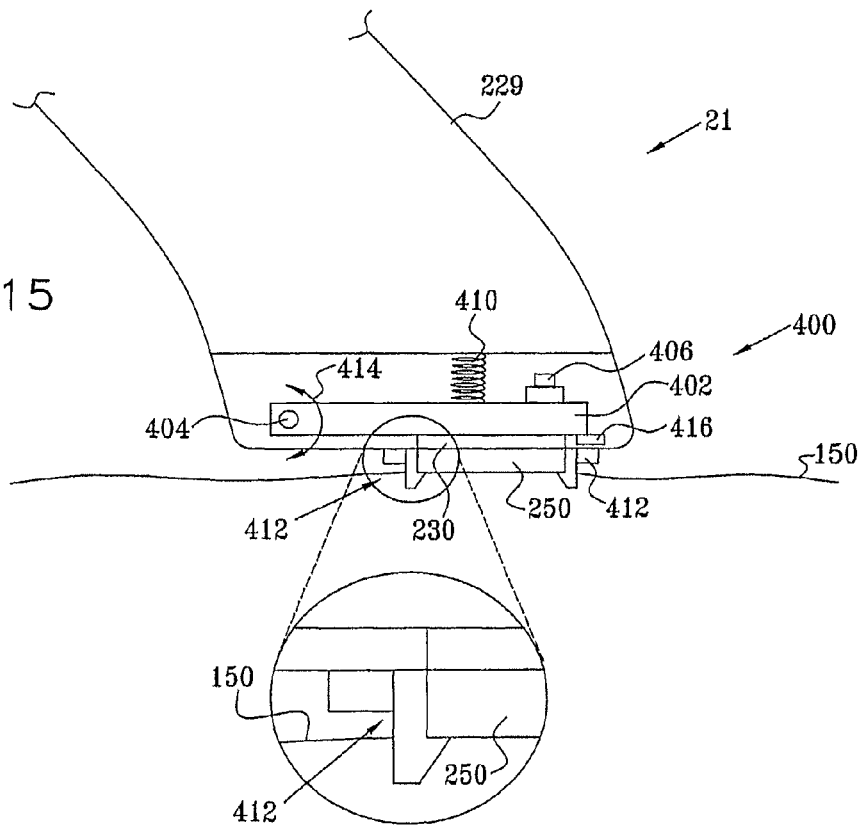
FIG. 15 is a schematic sectional illustration of a pressure-sensing mechanism for use with the devices shown in FIGS. 1, 2A, 3A, and 4A, in accordance with a preferred embodiment of the present invention.

FIG. 15 is a schematic sectional illustration of a pressure-sensing mechanism 400 for use with the devices described with reference to FIGS. 1, 2A, 3A, and 4A, in accordance with a preferred embodiment of the present invention. For simplicity of description, pressure-sensing mechanism 400 is described herein with reference to handheld device 21, described hereinabove with reference to FIGS. 3A, 3B and 3C, although the pressure-sensing mechanism applies equally well to the devices described with reference to FIGS. 1, 2A and 4A. Pressure-sensing mechanism 400 is used to provide an indication that firm contact has been made between electrode cartridge 250 and skin 150 of the subject, responsive to which indication an ablation procedure is begun.

Pressure-sensing mechanism 400 comprises a floating element 402, coupled to handle 229 by a pivot joint 404, which allows the floating element to pivot in the rotational directions indicated by arrow 414. Contact board 230 is fixed to the lower surface of floating element 402. Electrode cartridge 250 is removably coupled to contact board 230 using clips, such as snaps 412. The snaps are adapted to prevent the electrode cartridge from separating from contact board 230 (as would otherwise typically occur because of the force of gravity), while generally not applying any upward pressure on the electrode cartridge A spring 410 applies downward pressure on floating element 402. As a result, when the electrode cartridge is not in firm contact with the skin, floating element 402 pivots (shown as clockwise pivoting in FIG. 15) until the end of the floating element furthest from pivot joint 404 comes in contact with and is prevented from further pivoting by a stop element 416 fixed to handle 229. When electrode cartridge 250 is brought in contact with skin 150, and downward pressure is applied by the electrodes against skin 150, floating element 402 is pushed upward, activating a switch 406 on the floating element or elsewhere on the apparatus provided in this embodiment. As a result, a signal is generated indicating that firm contact has been made between electrode cartridge 250 and skin 150. Typically, switch 406 comprises a simple on-off switch or a general-purpose force transducer.

Figure 16:
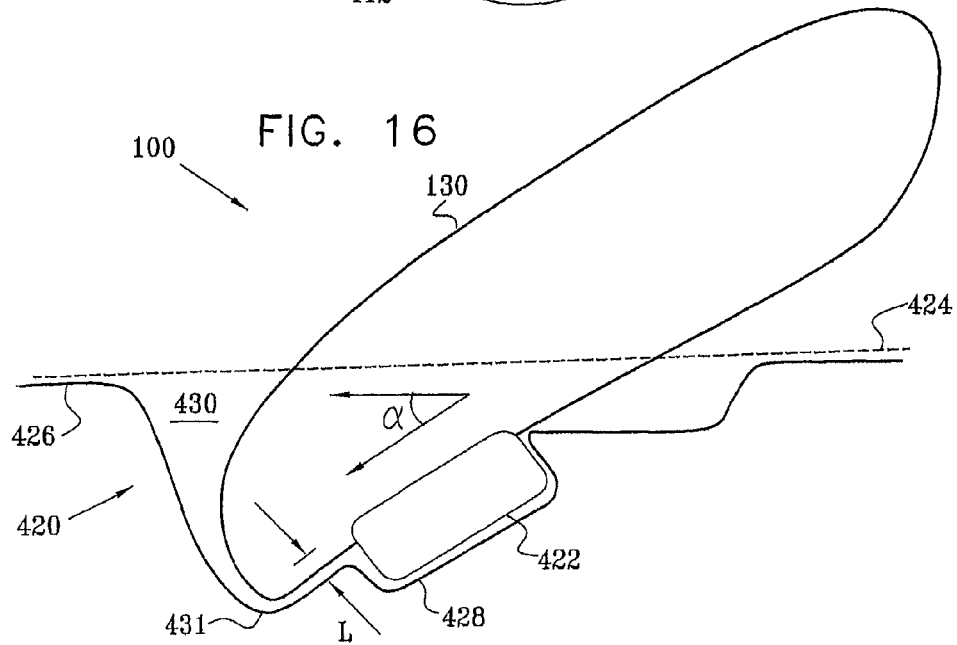
FIG. 16 is a schematic sectional illustration of packaging for storing an electrode-containing element, in accordance with a preferred embodiment of the present invention.

FIG. 16 is a schematic sectional illustration of packaging 420 for storing an electrode-containing element 422, in accordance with a preferred embodiment of the present invention. For simplicity of description, packaging 420 is described herein with reference to handheld device 100, described hereinabove with reference to FIG. 1, although packaging 420 can be used equally well in conjunction with the devices described hereinabove with reference to FIGS. 2A, 3A and 4A.

Packaging 420 comprises a container 426, preferably comprising blister packaging. Container 426 is shaped so as to define a first indentation 428, adapted to store a single electrode-containing element 422, such as an electrode cartridge 250, described hereinabove with reference to FIGS. 3A, 3B and 3C, or an electrode board 30, described hereinabove with reference to FIGS. 2A, 2B and 4A. Indentation 428 has a shape similar to electrode-containing element 422, such that the element sits securely in the indentation. Electrode-containing element 422 protrudes from indentation 428 by a distance of L, which is a sufficient distance to allow the element to couple to the handle. For example, L may be between about 1 and about 5 mm. To close the packaging, container 426 is covered with a removable covering 424. A second indentation 431 accepts the handle, thereby guiding the handle to accurately and firmly couple with electrode-containing element 422. Second indentation 431 is positioned so that the plane formed by the electrodes of electrode-containing element 422 and the plane formed by covering 424 form an angle alpha, the angle typically between 5 and 90 degrees, preferably between about 10 and 35 degrees. The angle is preferably configured to facilitate easy grasping of the handle by a user during removal of electrode-containing element 422 from packaging 420, given that electrode-containing element 422 does not protrude from packaging 420.

In order to attach electrode-containing element 422 to handle 130 (or contact board 230, as the case may be), covering 424 is removed by the user. Handle 130 is inserted into an open area 430 of packaging 420 and positioned substantially at angle alpha to the plane formed by covering 424 prior to its removal. The handle is then brought in contact with the top of electrode-containing element 422, and pressure is applied, which couples the handle to the electrode-containing element. The handle is then removed from the packaging.

Figure 17A:
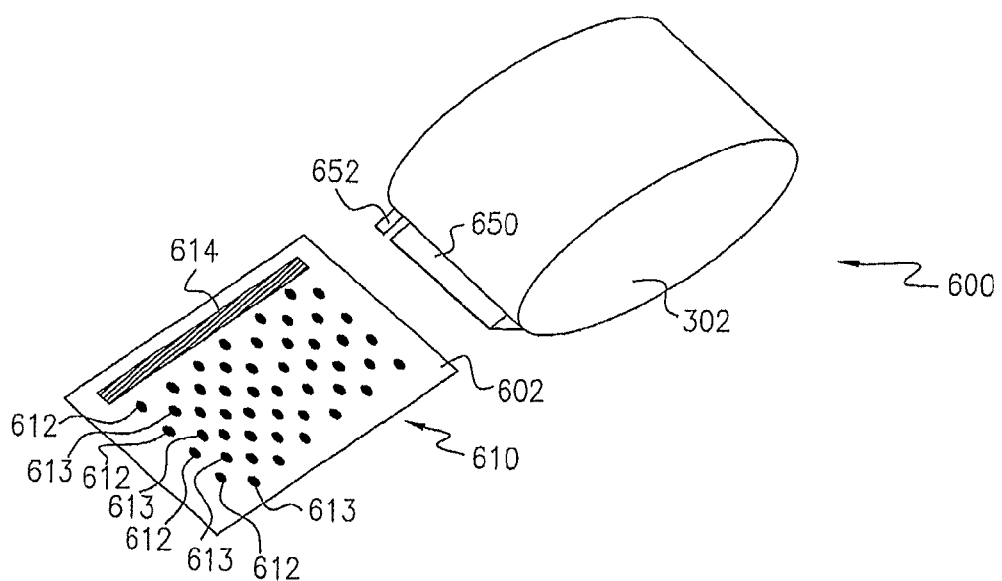
FIGS. 17A and 17B are schematic illustrations of yet another handheld device for facilitating transdermal transport of a substance, in accordance with a preferred embodiment of the present invention.
Figure 17B:
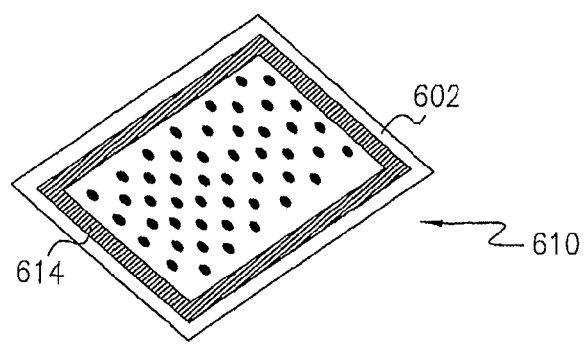

FIGS. 17A and 17B are schematic illustrations of apparatus 600 for enabling transdermal transport of a substance, such as a drug, in accordance with a preferred embodiment of the present invention. Except for differences described hereinbelow, apparatus 600 is preferably configured to operate generally in accordance with techniques described herein for ablating stratum corneum.

Preferably, a handheld unit including at least one high-voltage driving electrode 650, a return electrode 652, and a power source (not shown) is passed by the user over an electrode cartridge 602, which typically comprises a set of monopolar receiving electrodes 610 and a return strip 614. Electrodes 610 and return strip 614 preferably pass through electrode cartridge 602 from the top surface thereof (FIG. 17A) to the bottom surface thereof (FIG. 17B), so as to contact skin 150 when the electrode cartridge is placed on the skin. Alternatively, the electrodes are configured by other means to electrically connect the top and bottom surfaces of electrode cartridge 602. In this manner, as the handheld unit is passed over the electrode cartridge, driving electrode 650 preferably comes into contact with each of receiving electrodes 610, and drives current through these electrodes into skin 150. Simultaneously, return electrode 652 makes contact with return strip 614 on electrode cartridge 602, allowing current injected into skin 150 to return to the handheld unit. Preferably, the current is configured so as to produce local ablation at the contact sites of each of electrodes 610 with skin 150. There is typically no substantial heating where return strip 614 contacts the skin, because the strip preferably has a significantly larger contact area than the total contact area of each of electrodes 610.

For some applications, the location of each of electrodes 610 on electrode cartridge 602 is arranged such that as the handheld unit is passed over the electrode cartridge, driving electrode 650 makes simultaneous contact with a desired number of electrodes 612 before contacting a subsequent group of one or more electrodes 613. Thus, as appropriate, electrodes 610 may be arranged in: (a) a staggered grid (FIGS. 17A and 17B), (b) a rectangular grid, with one or more electrodes in each dimension, or (c) a line parallel to return strip 614, so as to allow only one electrode to be contacted at a time. Alternatively or additionally, other geometries are used so as to provide contact, at any given time, between one or more of electrodes 610 and driving electrode 650.

Preferably, the shape of the surface of electrode cartridge 602 is configured in accordance with the desired motion of the handheld unit. For example, return strip 614 may be recessed into the surface of the electrode cartridge, in a manner which facilitates desired contact between the handheld unit and the electrode cartridge.

If appropriate, the power source may be configured to apply the current such that two or more passes of the handheld unit over the electrode cartridge produce the desired extent of ablation of the stratum corneum. It is noted that although the handheld unit is shown in FIGS. 17A and 17B as being configured for manual operation, automated means may also be provided for moving driving electrode 650 over each of electrodes 610 on electrode cartridge 602.

For some applications, a drug to be applied through the skin is incorporated into apparatus 600, e.g., around electrodes 610. Alternatively, the drug may be applied to the skin following treatment of the skin and removal of electrode cartridge 602 therefrom, e.g., by means of a standard medicated patch placed on the treated region.

Figure 18:
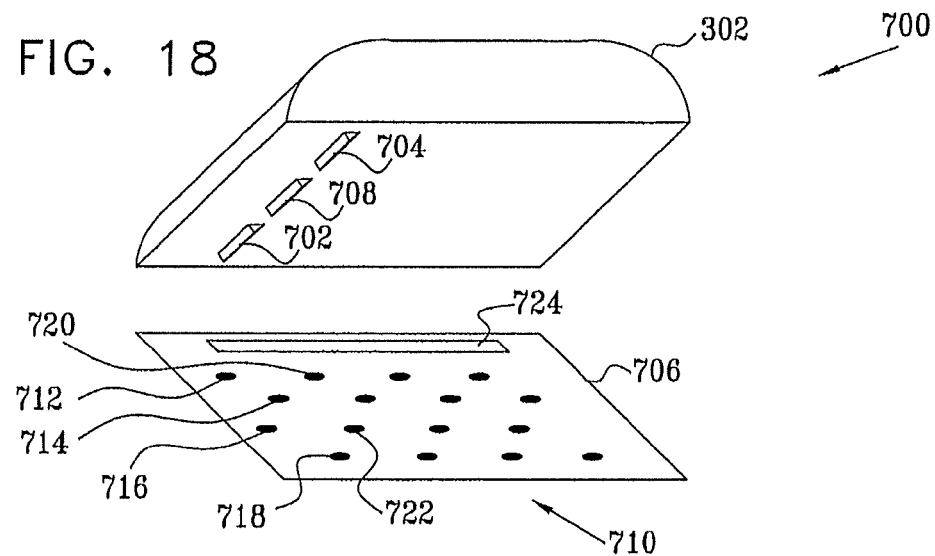
FIG. 18 is a schematic illustration of still another handheld device for facilitating transdermal transport of a substance, in accordance with a preferred embodiment of the present invention.

FIG. 18 is a schematic illustration of a device 700 for enabling transdermal transport of a substance, such as a drug, in accordance with a preferred embodiment of the present invention. Except for differences described hereinbelow, device 700 is preferably configured to operate generally in accordance with techniques described herein for ablating stratum corneum.

Device 700 functions in a similar manner to device 600 of FIG. 17A, except that whereas device 600 typically comprises a single driving electrode 650 (FIG. 17A), device 700 comprises at least two driving electrodes 704 and 708. Although only two driving electrodes are shown in FIG. 18, it is to be understood that a greater number of driving electrodes, such as up to 10 or up to 100, are appropriate for many applications. The multiple driving electrodes allow for more control over the activation of individual electrodes that are in contact with the skin. Device 700 additionally comprises a return electrode 702, a power source (not shown), and an electrode cartridge 706, which typically comprises an electrode array 710 and a return strip 724.

In a preferred embodiment, electrode 708 is activated on a first pass of device 700 over electrode cartridge 706, while electrode 704 is activated on a subsequent pass of device 700 over electrode cartridge 706. Partial activation of electrode array 710 reduces the instantaneous power requirement of device 700, which is important for battery-powered devices, as batteries are limited in the current and voltage they can deliver at any given moment.

Additionally, by stimulating only a limited number of electrodes at any given time, the sensation felt by the patient can be reduced. Reducing the sensation felt by a patient is achieved by limiting the density of stimulated electrodes at any given instant. Staggered electrode array 710 and multiple driving electrodes 704 and 708 have the effect of reducing the number and density of simultaneously stimulated electrodes. For example, during a first pass of device 700 over array 706, driving electrode 708 is activated while driving electrode 704 is not activated. Thus, ablation electrode 712 is activated first, followed by electrode 714, to be followed by electrode 720, et cetera, such that only one electrode is activated at a time. Similarly, on the second pass, driving electrode 704 is activated while electrode 708 is not activated, resulting in the sequence of stimulated electrodes 716, 718, 722, et cetera. Typical electrode cartridges 706 have many more electrodes than shown in FIG. 18, but the same principle is preferably applied to reduce instantaneous power requirements and the concentration of stimulated electrodes.

For some applications, electrode contacts on one side of electrode cartridge 706 are coupled to electrodes on the other side, in a configuration that generally maximizes the distance between sequentially-activated electrodes (e.g., using techniques described hereinabove with respect to traces and vias in a multi-layer PCB, applied here to electrode cartridge 706). In this case, only one pass is typically utilized.

Figure 19:
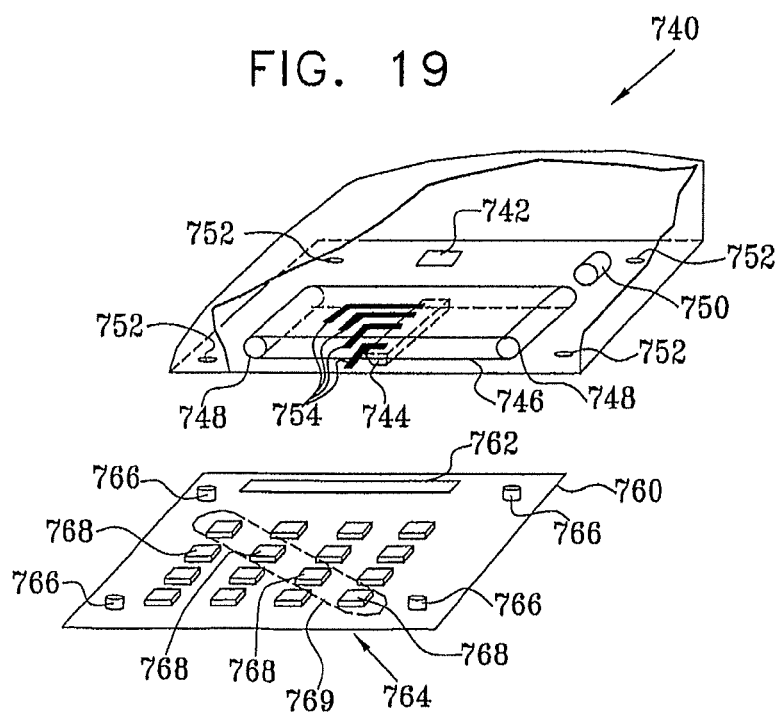
FIG. 19 is a schematic, partly sectional illustration of a further handheld device for facilitating transdermal transport of a substance, in accordance with a preferred embodiment of the present invention.

FIG. 19 is a schematic illustration of a device 740 for enabling transdermal transport of a substance, such as a drug, in accordance with a preferred embodiment of the present invention. Except for differences described hereinbelow, device 740 is preferably configured to operate generally in accordance with techniques described herein for ablating stratum corneum.

Device 740 functions in a similar manner to device 700 of FIG. 18, but while device 700 is moved manually, device 740 is automated. Device 740 comprises several mating holes 752, which fit over corresponding mating pegs 766 on an electrode cartridge 760, to ensure proper alignment of the two parts. Preferably, the top of electrode cartridge 760 comprises a return strip 762 and an array 764 of electrode pads 768, which couple to conductors (not shown) on the bottom of electrode cartridge 760. The conductors comprises either contacts, as described hereinabove with reference to FIGS. 2A and 4A, or ablation electrodes, as described hereinabove with reference to FIG. 3A. In the latter case, device 740 preferably comprises an electrode cartridge similar to electrode cartridge 250, described hereinabove with reference to FIG. 3A, which cartridge is removably coupled to the device. Device 740 additionally comprises a return electrode 742 and a power source (not shown).

Pads 768 serve as connectors between a plurality of driving electrodes 754 and the conductors. Driving electrodes 754 are preferably coupled to a manifold 744, such that the terminal ends of driving electrodes 754 come in contact with a diagonal line of pads 768, for example diagonal line 769, which has the effect of reducing the density of stimulated electrodes at any instant. This reduces the sensation felt by the patient during treatment with device 740, as described hereinabove. Alternatively, a staggered pattern of pads 768 is contacted by driving electrodes 754 at a given moment of time. Preferably, driving electrodes 754 comprise brush electrodes, which make electrical contact with pads 768.

It will be appreciated that a variety of arrangements of contact pads and driving electrodes may be utilized, and that the particular configuration shown in FIG. 19 is by way of illustration and not limitation. In addition, although for simplicity only sixteen contact pads 768 are shown in the figure, a larger number (e.g., 240) is preferably used, arranged in an array appropriate for a particular application, such as 4×60, or 12×20. In turn, each of the contact pads is preferably coupled to more than one conductor on the lower surface of electrode cartridge 760. In one preferred embodiment, each pad 768 is directly coupled to four conductors.

Manifold 744 is preferably coupled to a driving mechanism such as a belt 746, which is disposed around two cylinders 748. A motor 750 is coupled to one of cylinders 748, so as to cause movement of belt 746 and of driving electrodes 754. To effect the desired movement of driving electrodes 754 over pads 768, a control unit (not shown) is preferably used to activate and control motor 750. In a preferred embodiment, the control unit selectively activates one or more of driving electrodes 754 during each pass of the driving electrodes over pads 768, such that after one or more passes substantially all of the conductors have been activated. As described hereinabove, only one or a portion of the driving electrodes are typically activated at any one time, so as to reduce the instantaneous power requirements of the device and to minimize sensation felt by the patient.

Preferably, methods and apparatus described in U.S. patent application Ser. No. 09/859,645 to Avrahami and Sohn, entitled, "Monopolar and bipolar current application for transdermal drug delivery and analyte extraction," filed May 17, 2001, which is assigned to the assignee of the present patent application and is incorporated herein by reference, are utilized in combination with the methods and apparatus described herein.

It is noted that the figures depicting preferred embodiments of the present invention are not necessarily drawn to scale, and, instead, change certain dimensions in order to more clearly demonstrate some aspects of the invention.

It is further noted that whereas preferred embodiments of the present invention are generally described herein with respect to ablating the stratum corneum to facilitate substance delivery, the scope of the present invention includes ablating the stratum corneum so as to facilitate analyte extraction.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for ablating stratum corneum, comprising:
   a housing;
   a set of two or more wires coupled to and supported by the housing so as not to touch each other, each wire having two ends, each end defining an electrode; and
      an intermediate portion coupled to a coupling element; and
   wherein each of the wires is bent so that both electrodes of one wire together with the electrodes of at least the other wire substantially form a plane; and
   wherein the electrodes are configured to function as electrodes for ablating stratum corneum of skin of a subject when applied to the skin.

2. Apparatus according to claim 1, wherein each wire has a shape generally like a parabola.

3. Apparatus according to claim 1, wherein each wire is adapted to be supported by the housing by passing through the housing, and wherein a portion of each wire that passes through the housing is shaped so as to define an angular bend within the housing.

4. The apparatus according to claim 1, wherein each of the electrodes is configured to have a contact area with the skin characterized by a diameter of 10-150 microns.

5. The apparatus according to claim 4, wherein each of the electrodes is configured to have a contact area with the skin characterized by a diameter of 60-100 microns.

6. The apparatus according to claim 1, further comprising a control unit configured to ablate the stratum corneum by driving a current into the stratum corneum via the electrodes.

7. The apparatus according to claim 6, wherein the control unit is configured to detect electrical impedance of the stratum corneum, and to terminate driving the current in response thereto.

8. The apparatus according to claim 6, wherein the control unit is configured to ablate the stratum corneum by driving the current for a fixed length of time, determined in advance to be sufficient to achieve a desired degree of ablation of the stratum corneum.

9. The apparatus according to claim 6, wherein the control unit is configured to ablate the stratum corneum by driving a current into the stratum corneum via the electrodes, the current having a frequency of between 10 kHz and 4000 kHz.

10. The apparatus according to claim 9, wherein the control unit is configured to ablate the stratum corneum by driving a current into the stratum corneum via the electrodes, the current having a frequency of between 50 kHz and 500 kHz.

11. The apparatus according to claim 1, wherein the number of the electrodes in each set is double the number of the wires in the set.

12. The apparatus according to claim 1, wherein the intermediate portion and the coupling element are also electrically coupled.

* * * * *